US007950396B2

(12) United States Patent
Rose et al.

(10) Patent No.: US 7,950,396 B2
(45) Date of Patent: May 31, 2011

(54) TREATMENT FOR OTITIS EXTERNA

(75) Inventors: Andreas Rose, San Marcos, CA (US); Nicholas G. Loebel, Woodinville, WA (US); Cale Street, Edmonds, WA (US); Roger Andersen, Ladysmith (CA)

(73) Assignee: Ondine International Holdings Ltd., St. Michael (BB)

( * ) Notice: Subject to any disclaimer, the term of this patent is extended or adjusted under 35 U.S.C. 154(b) by 1068 days.

(21) Appl. No.: 11/741,604

(22) Filed: Apr. 27, 2007

(65) Prior Publication Data
US 2008/0119914 A1 May 22, 2008

Related U.S. Application Data

(60) Provisional application No. 60/866,897, filed on Nov. 22, 2006, provisional application No. 60/796,345, filed on Apr. 28, 2006.

(51) Int. Cl.
*A61B 19/00* (2006.01)
(52) U.S. Cl. .......................................... 128/898; 607/88
(58) Field of Classification Search ............. 607/88–92, 607/136, 135; 128/898
See application file for complete search history.

(56) References Cited

U.S. PATENT DOCUMENTS

| | | | |
|---|---|---|---|
| 5,611,793 A | 3/1997 | Wilson et al. | |
| 6,211,335 B1 | 4/2001 | Owen et al. | |
| 6,251,127 B1 | 6/2001 | Biel | |
| 6,389,313 B1 * | 5/2002 | Marchitto et al. ............. | 604/21 |
| 6,551,346 B2 | 4/2003 | Crossley | |
| 6,583,117 B2 | 6/2003 | Owen et al. | |
| 6,602,274 B1 | 8/2003 | Chen | |
| 6,607,522 B1 | 8/2003 | Hamblin et al. | |
| 6,622,049 B2 | 9/2003 | Penner et al. | |
| 7,494,487 B2 * | 2/2009 | Timm ........................... | 604/514 |
| 7,559,945 B2 * | 7/2009 | Breden et al. ................... | 607/88 |
| 2003/0180224 A1 | 9/2003 | Brown et al. | |
| 2004/0147508 A1 | 7/2004 | Brown et al. | |
| 2005/0107853 A1 | 5/2005 | Krespi et al. | |
| 2006/0047329 A1 | 3/2006 | Krespi et al. | |
| 2006/0093561 A1 | 5/2006 | Kennedy | |
| 2006/0194164 A1 | 8/2006 | Altshuler et al. | |
| 2007/0162092 A1 * | 7/2007 | Yen ................................ | 607/89 |
| 2007/0238747 A1 * | 10/2007 | van Duzer et al. ............ | 514/279 |

(Continued)

FOREIGN PATENT DOCUMENTS

RU 2235568 9/2004

(Continued)

OTHER PUBLICATIONS

Copending U.S. Appl. No. 11/741,627, filed Apr. 27, 2007.

(Continued)

*Primary Examiner* — Ahmed M Farah
(74) *Attorney, Agent, or Firm* — Dobrusin & Thennisch PC

(57) ABSTRACT

The present invention presents devices, kits, systems and methods that can be used to otitis externa. For example, a method of present invention includes applying a photosensitizing composition to treatment site within ear cavity where microbes causing otitis externa are located; inserting at least a portion of a light delivery device into the cavity; and applying light to the treatment site at a wavelength absorbed by the photosensitizing composition so as to inhibit or eliminate the microbes and/or to reduce inflammation at the treatment site but without causing physiological damage to host tissue within the ear cavity; wherein the light is delivered by the light delivery device to the treatment site and the light delivery device is in light communication with a light source via a waveguide.

4 Claims, 19 Drawing Sheets

U.S. PATENT DOCUMENTS

2007/0255356 A1* 11/2007 Rose et al. .................. 607/88
2007/0255357 A1* 11/2007 Rose et al. .................. 607/88
2008/0208297 A1* 8/2008 Gertner et al. .............. 607/92

FOREIGN PATENT DOCUMENTS

WO  WO2006/632847  3/2006
WO  WO2006/115761  11/2006

OTHER PUBLICATIONS

Copending U.S. Appl. No. 11/741,584, filed Apr. 27, 2007.
www.puritanmedproducts.com Product Nos. 4545 and 4620, 2 pages, Oct. 19, 2007.
http://www.emedicine.com/ent/topic362.htm, Billings, Kathleen R., Ototopical Antibiotics, Last Updated Mar. 21, 2001, 9 pages.

* cited by examiner

TREATMENT FOR OTITIS EXTERNA

CLAIM OF BENEFIT OF FILING DATE

This application claims the benefit of U.S. Provisional Application Ser. No. 60/796,345 titled: "Photodisinfection Delivery Device" filed on Apr. 28, 2006 and U.S. Provisional Application Ser. No. 60/866897 titled: "Treatment for Otitis Externa" filed on Nov. 22, 2006.

FIELD OF INVENTION

The present invention provides photodisinfection devices, kits, systems and methods to treat otitis externa.

BACKGROUND OF THE INVENTION

Sources of infective microbes are prevalent throughout our environment. A body cavity is naturally colonized with an enormous number of microbes usually kept in check by normal metabolism and an intact immune system. With the breakdown of the immune system, microbes cause infections. Antibiotics are generally used to treat such infections, but many microbes are becoming resistant to antibiotic treatments. Accordingly, there is a need to treat infections and decolonize microbes residing in body cavities without the use of antibiotics.

SUMMARY OF THE INVENTION

Photodisinfection can meet the need to treat infections and decolonize microbes residing in body cavities without the use of antibiotics. Photodisinfection is the use of a photosensitizing composition activated by light to inhibit or eliminate microbes. The present invention presents devices, kits, systems and methods that can be used to deliver and/or activate a photosensitizing composition in any cavity including a body cavity for which photodisinfection is desired. The present invention can be used for humans and other animals. The present invention can also be used for photodisinfection of inanimate objects.

The present invention provides a device for photodisinfection of a cavity comprising: a member having a base portion, an insert portion adapted for insertion into the cavity, and a pocket adapted for communication with a waveguide which is connected to a light source for delivering light to the device, wherein the pocket includes a light dispersing section that is adapted for light communication with distal end of the waveguide and desired illumination pattern for photodisinfection of the cavity is provided by at least one of the elements selected from the group consisting of: surface finish of the light dispersing section, geometry of the light dispersing section, surface finish of the member, geometry of the member, and a combination thereof.

The present invention further provides a treatment system for photodisinfection of a cavity comprising: a device comprising a member having a base portion, an insert portion adapted for insertion into the cavity, and a pocket adapted for communication with a waveguide which is connected to a light source for delivering light to the device, wherein the pocket includes a light dispersing section that is adapted for light communication with distal end of the waveguide; the waveguide; and the light source; wherein desired illumination pattern for photodisinfection of the cavity is provided by at least one of the elements selected from the group consisting of: surface finish of the light dispersing section, geometry of the light dispersing section, surface finish of the member, geometry of the member, surface finish of distal end of the waveguide, geometry of the waveguide, and a combination thereof The present invention provides a treatment kit for photodisinfection of a cavity comprising: a device comprising a member having a base portion, an insert portion adapted for insertion into the cavity, and a pocket adapted for communication with a waveguide which is connected to a light source for delivering light to the device, wherein the pocket includes a light dispersing section that is adapted for light communication with distal end of the waveguide and desired illumination pattern for photodisinfection of the cavity is provided by at least one of the elements selected from the group consisting of: surface finish of the light dispersing section, geometry of the light dispersing section, surface finish of the member, geometry of the member, and a combination thereof; a photosensitizing composition contained in a fluid source; and an application tip.

The present invention further provides a method of photodisinfection of a cavity comprising: providing a device comprising: a member having a base portion, an insert portion adapted for insertion into the cavity, and a pocket adapted for communication with a waveguide which is connected to a light source for delivering light to the device, wherein the pocket includes a light dispersing section that is adapted for light communication with distal end of the waveguide and desired illumination pattern for photodisinfection of the cavity is provided by at least one of the elements selected from the group consisting of: surface finish of the light dispersing section, geometry of the light dispersing section, surface finish of the member, geometry of the member, surface finish of distal end of the waveguide, geometry of the waveguide, and a combination thereof; applying a photosensitizing composition to treatment site within the cavity; inserting at least a portion of the insert portion into the cavity; and applying light delivered by the device from the light source and via the waveguide to the treatment site within the cavity at a wavelength absorbed by the photosensitizing composition so as to inhibit or eliminate microbes located at the treatment site.

The present invention provides a device for nasal decolonization of microbes comprising: a base portion, an insert portion adapted for insertion into a nasal cavity and has a surface finish comprising of ribs, a pocket adapted for communication with a waveguide and has a light dispersing section having a geometry of a hemisphere with an apex cone.

The present invention further provides a method for nasal decolonization of microbes comprising: providing a device comprising: a member comprising: a base portion, an insert portion adapted for insertion into a nasal cavity and has a surface finish comprising of ribs, a pocket adapted for communication with a waveguide and has a light dispersing section having a geometry of a hemisphere with an apex cone; applying a photosensitizing composition to anterior nares; inserting at least a portion of the insert portion into the nasal cavity; and applying light delivered by the device from a light source via the waveguide to the anterior nares at a wavelength absorbed by the photosensitizing composition so as to inhibit or eliminate microbes located at the anterior nares but without causing physiological damage to host tissue within the nasal cavity.

The present invention further provides a method of treating otitis externa comprising: applying a photosensitizing composition to treatment site within ear cavity where microbes causing otitis externa are located; inserting at least a portion of a light delivery device into the cavity; and applying light to the treatment site at a wavelength absorbed by the photosensitizing composition so as to inhibit or eliminate the microbes and/or to reduce inflammation at the treatment site but without causing physiological damage to host tissue within the ear cavity; wherein the light is delivered by the light delivery device to the treatment site and the light delivery device is in light communication with a light source via a waveguide, and the application of light step does not cause physiological damage to host tissue within the ear cavity.

The present invention further provides a method for nasal decolonization of microbes comprising: applying a photosensitizing composition comprising methylene blue to anterior nares; inserting at least a portion of a light delivery device into the nasal cavity; and applying light to the anterior nares at a wavelength ranges from about 650 nm to 680 nm and without causing physiological damage to host tissue within the nasal cavity; wherein the light is delivered by the light delivery device to the anterior nares; the light delivery device is in light communication with a light source via a waveguide; and over 90% of the microbes at the anterior nares is eliminated by the nasal decolonization.

The present invention provides methods for treatment of MRSA, *E. coli*, and *E. fecalis* comprising: applying a photosensitizing composition comprising methylene blue to the treatment site where the MRSA, *E. coli*, and/or *E. Fecalis* are located; applying light to the treatment site at a wavelength ranges from about 650 nm to 680 nm; wherein the light is delivered by the light delivery device to the treatment site; the light delivery device is in light communication with a light source via a waveguide; and over 90% of the MRSA, *E. coli*, and/or *E. Fecalis* at the treatment site is eliminated by the treatment method.

BRIEF DESCRIPTION OF THE DRAWINGS

The features and inventive aspects of the present invention will become more apparent upon reading the following detailed description, claims, and drawings, of which the following is a brief description:

DESCRIPTION OF THE PREFERRED EMBODIMENT

I. Definitions

Figure 1:
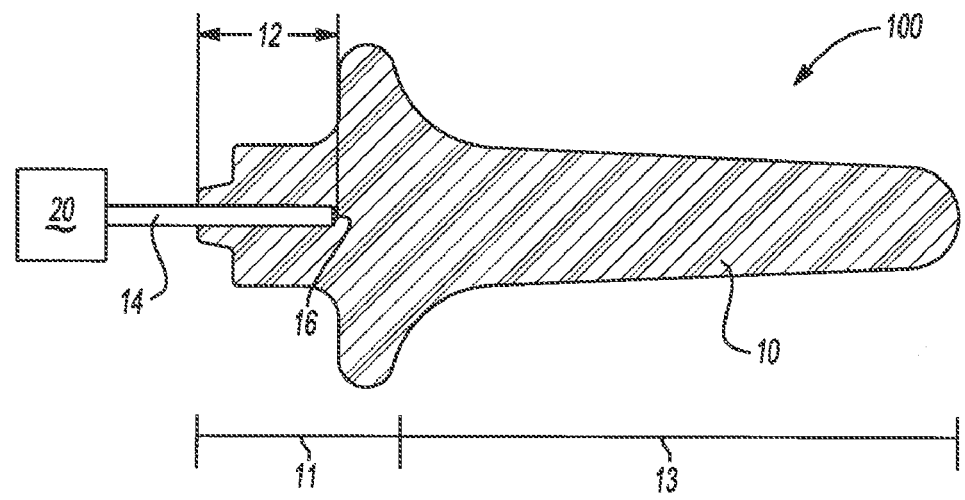
FIG. 1 is a sectional view of an exemplary device according to the present invention.
Figure 2:
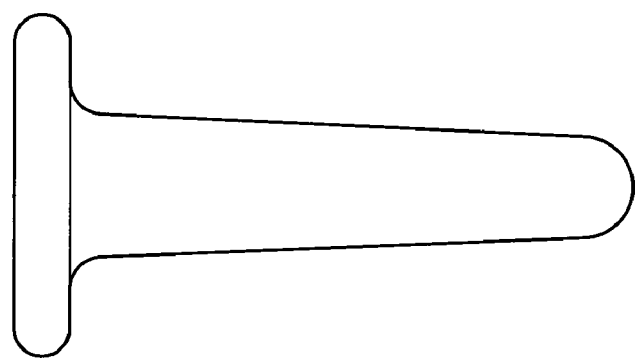
FIG. 2 is a side view of one exemplary embodiment of the member of the device shown in FIG. 1.
Figure 3:
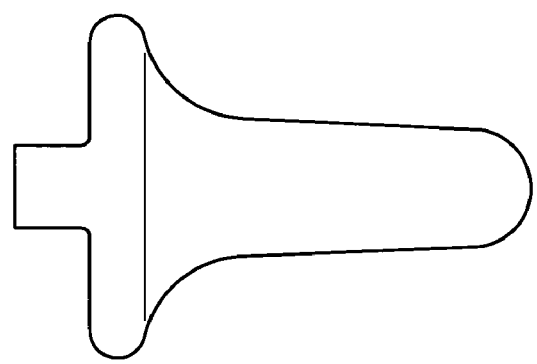
FIG. 3 is a side view of another exemplary embodiment of the member of the device shown in FIG. 1.
Figure 4:
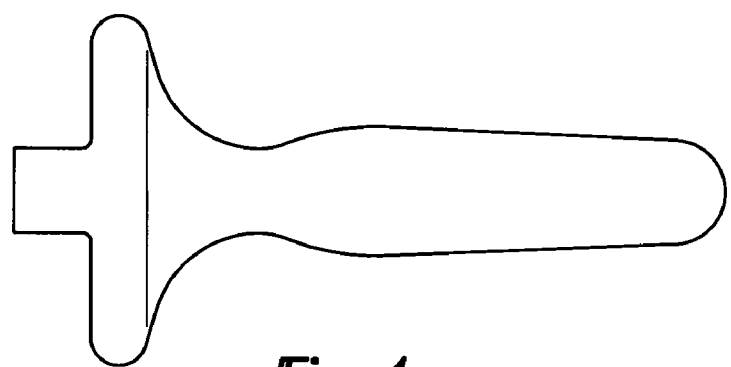
FIG. 4 is a side view of yet another exemplary embodiment of the member of the device shown in FIG. 1.
Figure 5:
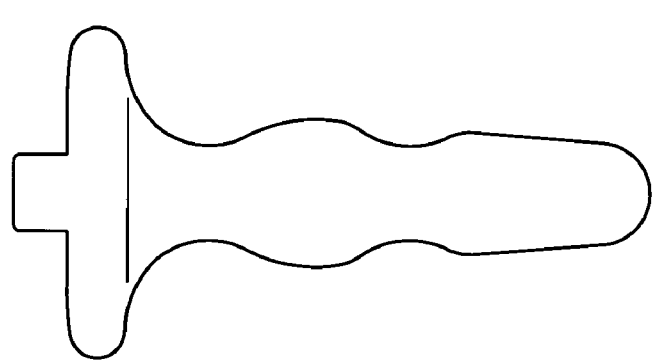
FIG. 5 is a side view of another exemplary embodiment of the member of the device shown in FIG. 1.
Figure 6:
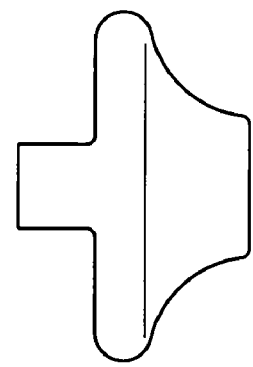
FIG. 6 is a side view of yet another exemplary embodiment of the member of the device shown in FIG. 1.

The following terms are intended to have the following general meanings as they are used herein:

1. Body cavity: any cavity within a body such as ear, nose, vagina, lung, the entire digestive track (e.g., throat, esophagus, stomach, intestines, rectum, etc.), gall bladder, bladder, any open wound or the like. The body cavity can be within a human body or a body of another animal.

2. Light: light at any wavelengths that can be absorbed by a photosensitizing composition. Such wavelengths include wavelengths selected from the continuous electromagnetic spectrum such as ultraviolet ("UV"), visible, the infrared (near, mid and far), etc. The wavelengths are generally between about 100 nm to 10,000 nm, with exemplary ranges between about 160 nm to 1600 nm, between about 400 nm to about 900 nm, and between about 500 nm to about 850 nm, although the wavelengths may vary depending upon the particular photosensitizing compound used and the light intensity. Depending on the application, the light produced may be a single wavelength or multiple wavelengths. The light may be produced by any suitable art-disclosed light emitting devices such as lasers, light emitting diodes ("LEDs"), arc lamps, incandescent sources, fluorescent sources, gas discharge tubes, thermal sources, light amplifiers or the like.

3. Light Source: a light emitting device such as laser, light emitting diode ("LEDs"), arc lamp, incandescent source, fluorescent source, gas discharge tube, thermal source, light amplifier, or a combination thereof. The output of the light source is preferably adjustable so that the operator can modify the wavelength, the power output, the size of illumination, or combinations thereof while carrying out the present method. For example, the wavelength of a laser may be adjusted to activate different photosensitizers in the photosensitizing composition. Alternately, the power of the light source may be increased or decreased after an application of light energy to the treatment area. In addition, the light source may comprise a temperature monitoring device so that over heating of the host tissues in and around the treatment area may be avoided. Suitable temperature monitoring devices may comprise an IR device, a fiber optic device, a thermocouple, or a combination thereof.

4. Microbes: any and all disease-related microbes such as virus, fungus, and bacteria including Gram-negative organisms, Gram-positive organisms or the like. Some examples of microbes include but are not limited to, *Staphylococcus aureus*, Methicillin-resistant *Staphylococcus aureus* ("MRSA"), *Escherichia coli* ("*E. coli*"), *Enterococcus fecalis* ("*E. fecalis*"), *Pseudomonas aeruginosa, Aspergillus, Candida*, etc.

5. Photosensitizing composition: a composition comprising at least one suitable art-disclosed photosensitizer that has at least an antimicrobial action upon application of electromagnetic energy of certain wavelength(s). Suitable photosensitizers include both Type I and Type II photosensitizers, where Type I photosensitizers produce a free radical upon the application of light and Type II photosensitizers produce singlet oxygen upon the application of light. While photosensitizers that have other modes of operation (e.g. generation of heat) are contemplated, those types discussed above are preferred. Suitable classes of compounds that may be used as antimicrobial photosensitizers include tetrapyrroles or derivatives thereof such as porphyrins, chlorins, bacteriochlorins, phthalocyanines, naphthalocyanines, texaphyrins, verdins, purpurins or pheophorbides, phenothiazines, etc., such as those described in U.S. Pat. Nos. 6,211,335; 6,583,117; and 6,607,522 and U.S. Patent Publication No. 2003-0180224. Preferred phenothiazines include methylene blue (MB), toluidine blue (TBO), and those discussed in U.S. Patent Publication No. 2004-0147508. Other preferred antimicrobial photosensitizers include indocyanine green (ICG). Combinations of two or more photosensitizers, such as MB and TBO or the like, are also suitable. The photosensitizer may be present in the photosensitizer composition in any suitable amounts. Examples are between about 0.001 percentage of total weight (wt %) and 10 wt %, between about 0.005 wt % and about 1 wt %, between about 0.01 wt % to about 0.5 wt %, and between about 0.02 wt % to about 0.1 wt %. The photosensitizing composition may optionally contain a therapeutic agent, which is any chemical, drug, medication, proteinaceous molecule, nucleic acid, lipid, antibody, antigen, hormone, nutritional supplement, cell or any combination thereof that helps ameliorate a condition. Preferred therapeutic agents include those that promote wound healing, have anti-inflammatory action, have antimicrobial action, and/or provide pain relief. The photosensitizing composition may also optionally contain carriers, diluents, or other solvents for the photosensitizer or other components of the composition and may be used to adjust the concentration of photosensitizer. The photosensitizing composition may be any suitable phase such as a liquid, gel, paste, putty, or solid. Preferably, the compositions has a viscosity low enough to flow into the treatment site while also having a viscosity high enough to maintain the composition within the treatment site. Further compositions that become liquid after application to the treatment site are contemplated such as those that melt or go into solution in the treatment site. Alternately, the composition may gel after application to the treatment site as a liquid; this would permit the composition to cover the treatment site effectively, while also maintaining the composition in the treatment site. The photosensitizers mentioned above are examples and are not intended to limit the scope of the present invention in any way.

II. Description of Exemplary Devices

A. Devices for Photodisinfection of the Nasal Cavity

FIG. 1 illustrates one exemplary embodiment of a device 100 according to the present invention. The device 100 enables photodisinfection of a cavity including human's nasal cavity. Many colonies of microbes reside around the entrance of the nasal cavity (i.e., anterior nares). The device 100 can provide illumination to desired surface areas of the nasal cavity (i.e., anterior nares) by providing a desired and/or optimized illumination pattern around the anterior nares.

Referring back to FIG. 1, the device 100 includes a member 10 having a base portion 11 and an insert portion 13 adapted for insertion into a body cavity (e.g., anterior nares). To avoid potential injury to a patient, it is preferred that at least the insert portion 13 does not contain any sharp corner and/or sharp edge. The member 10 can be constructed out of any suitable art-disclosed material that is transparent or translucent to the illumination wavelengths. Examples of such materials are plastic, epoxy, glass, or any other suitable biocompatible material. As an example, the member 10 can be made out of polycarbonate, acrylic or Poly(methyl methacrylate). The illumination pattern of the device 100 can be impacted by geometry and/or surface finish of the member 10. For example, the member 10 may include suitable art-disclosed surface finishes such as smoothness, roughness, ribs, inclusions, pigments, microspheres, facets, embossed patterns, or a combination thereof to modify the illumination pattern (e.g., light scattering or the like) during photodisinfection. FIGS. 2-6 illustrate some examples of alternative member 10.

The member 10 includes a pocket 12 adapted for communication with a waveguide 14, which is shown in FIG. 1 as an optical fiber. The optical fiber can be any suitable art-disclosed optical fiber such as a plastic fiber, a plastic clad glass fiber, a glass fiber, or the like. The optical fiber can be of any suitable size. Examples of suitable fiber size includes optical fiber that is greater than about 3 mm in diameter, from about 3 mm to about 1.5 mm in diameter, from about 1.5 mm to 400 um in diameter, from about 1 mm to 400 um in diameter; less than about 400 um in diameter, and less than about 200 um in diameter. Also, multiple fibers may be used as the waveguide 14. If desired, instead of a single termination, multiple fibers can have multiple terminations inside the member 10. The waveguide 14 may be attached to the member 10 via art-disclosed means. For example, the pocket 12 may have features that grip the waveguide 14 (e.g., inward pointing teeth that accepts the insertion of the waveguide 14 but resist its removal, threads, or the like). The waveguide 14 may also be held in by adhesive, mechanical deformation (e.g., crimping, heat staking), friction, or the like. Furthermore, the waveguide 14 may be designed to be removably attached to the member 10. For example, the end of the waveguide 14 may also be enclosed in a ferrule of some type. The ferrule can be constructed of any suitable art-disclosed material(s) such as ceramic, metal, or the like. The ferrule can be retained permanently or be removable. The ferrule may be part of the waveguide 14 or part of the member 10. Without limitation, various threaded engagements or "twist and lock" bayonets may be employed to retain the waveguide 14 until it is desired to remove it.

The waveguide 14 has a directional output of light at its distal end 16 and can deliver the illumination wavelength(s) desired for photodisinfection. Generally, the waveguide 14 can be employed to deliver light of any wavelength(s) including visible and invisible light. For example, the waveguide 14 can be employed for delivering light having wavelengths between and/or including deep UV to Far IR. The wavelengths are generally between about 100 nm to 10,000 nm, with exemplary ranges between about 160 nm to 1600 nm, between about 400 nm to about 800 nm, and between about 500 nm to about 850 nm, although the wavelengths may vary depending upon the particular photosensitizing compound used and the light intensity. Depending on the application, the light produced may be a single wavelength or multiple wavelengths. Also, depending on the desired illumination pattern, the waveguide distal end 16 can have a surface finishes such as smoothness, roughness, ribs, inclusions, pigments, microspheres, facets, embossed patterns, or a combination thereof; and have a range of different geometries such as flat, concave or convex conic (including all variants from full to truncated), hemisphere with an apex cone, or a combination thereof.

Figure 7:
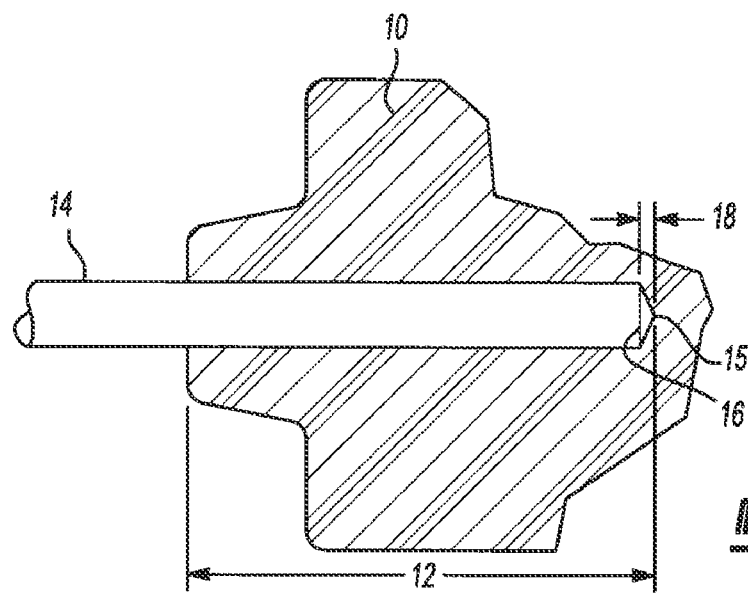
FIG. 7 illustrates a more detail view of the pocket of the device shown in FIG. 1.
Figure 8:
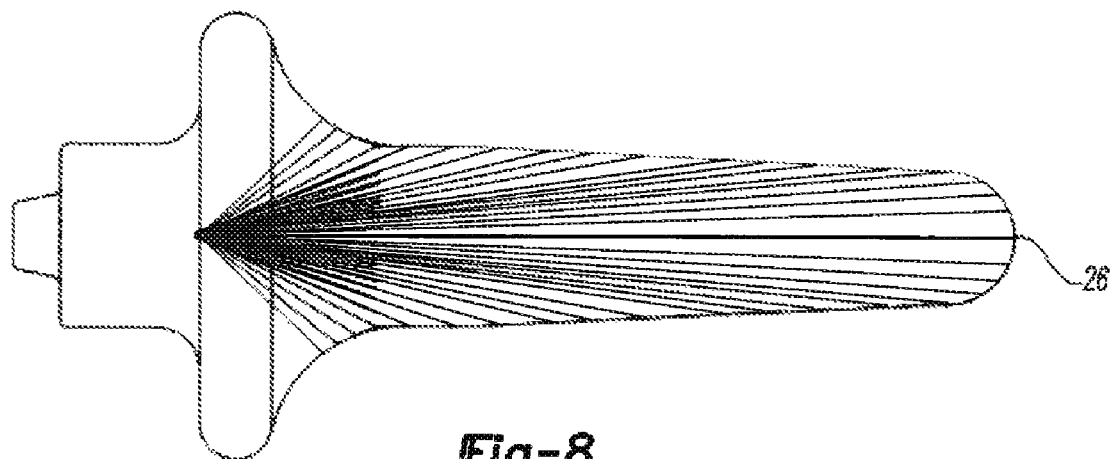
FIG. 8 illustrates an exemplary path of the light through the device shown in FIG. 1.

The pocket 12 of FIG. 1 is shown in greater detail in FIG. 7. The light dispersing section 18 at distal end 15 of the pocket 12 can assist in providing an illumination pattern desired for the photodisinfection. For example, for the nasal cavity, one embodiment of the dispersing section 18 is a cone shape allowing an illumination pattern as shown in FIG. 8. In FIG. 8, the balance of light leaking near the opening of the cavity compared to the light propagating to the distal end of the device 100 is depicted. Referring back to FIG. 7, the light dispersing section 18 may have a surface finish (e.g., smoothness, roughness, ribs, pigments, microspheres, Fresnel elements, deflective elements, reflective elements, facets, embossed patterns, or a combination thereof) that can further improve the redistribution of light and/or alter the illumination pattern. The surface finish and geometry of the light dispersing section 18, the surface finish and geometry waveguide distal end 16, and the surface finish and geometry of the member 10 can all interact together to provide the desired illumination pattern.

Figure 9:
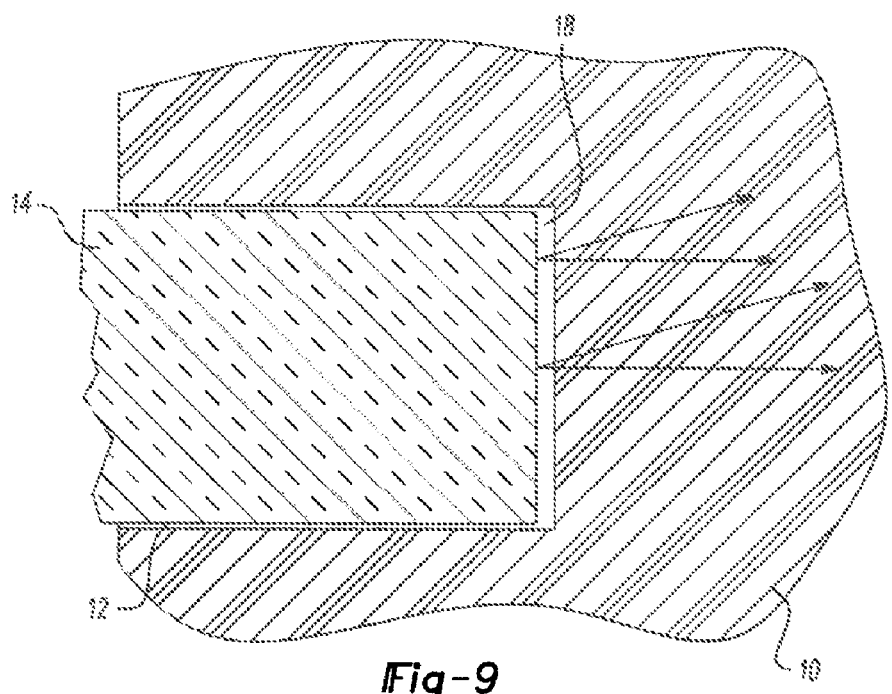
FIG. 9 is a side view of one exemplary embodiment of the light dispersing section of the pocket of the member of the device shown in FIG. 1.
Figure 10:
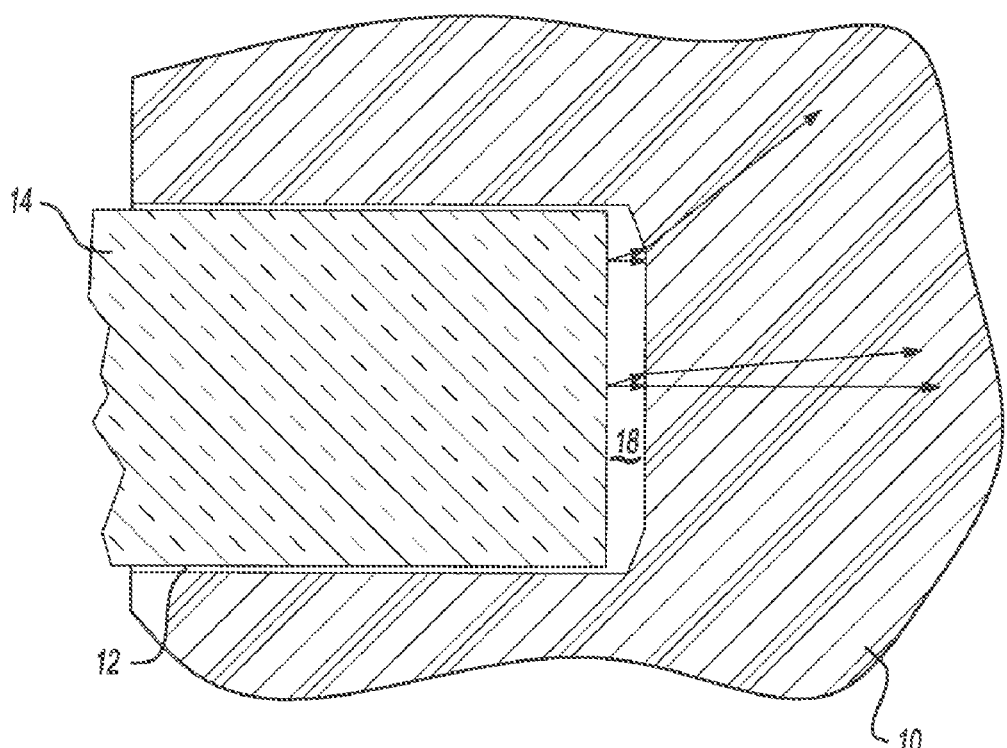
FIG. 10 is a side view of another exemplary embodiment of the light dispersing section of the pocket of the member of the device shown in FIG. 1.
Figure 11:
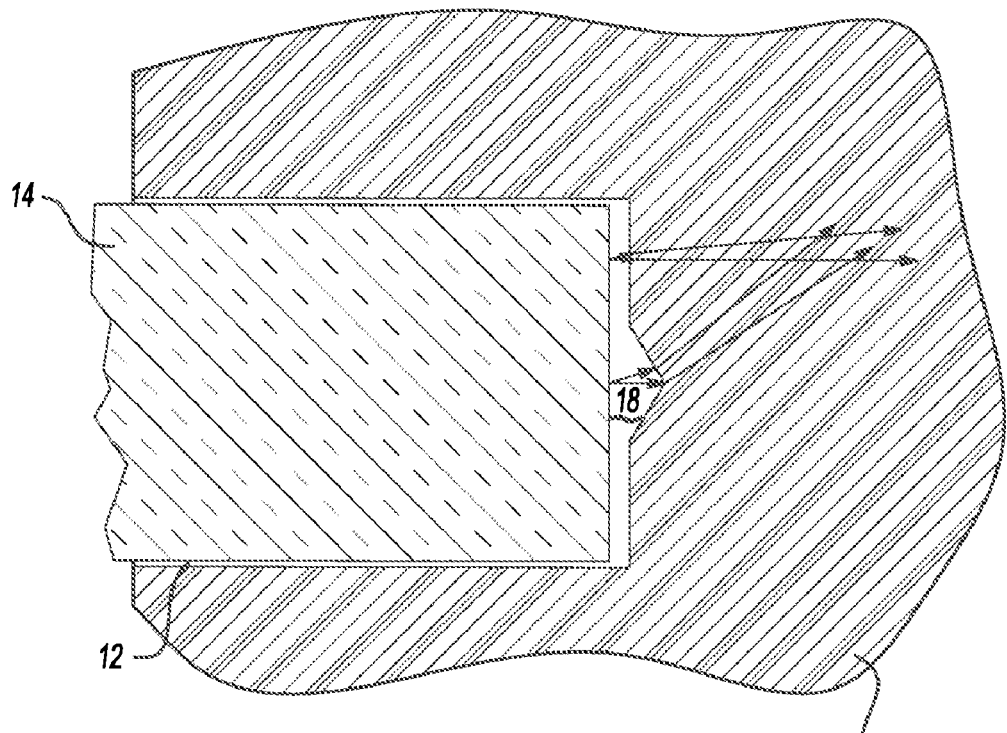
FIG. 11 is a side view of yet another exemplary embodiment of the light dispersing section of the pocket of the member of the device shown in FIG. 1.
Figure 12:
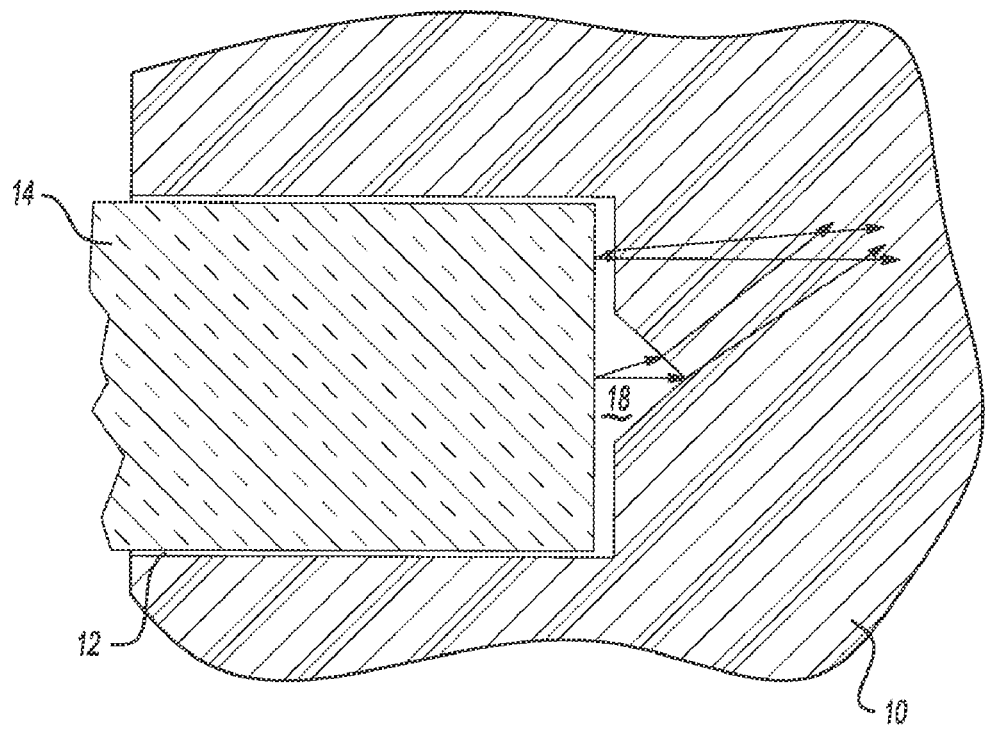
FIG. 12 is a side view of another exemplary embodiment of the light dispersing section of the pocket of the member of the device shown in FIG. 1.
Figure 13:
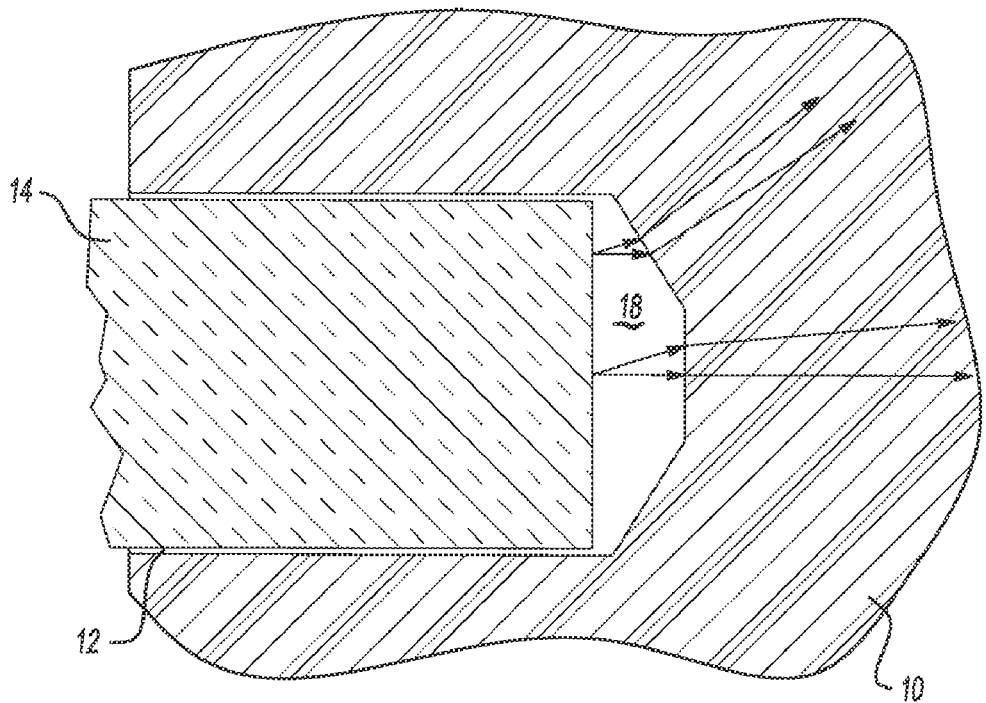
FIG. 13 is a side view of yet another exemplary embodiment of the light dispersing section of the pocket of the member of the device shown in FIG. 1.
Figure 14:
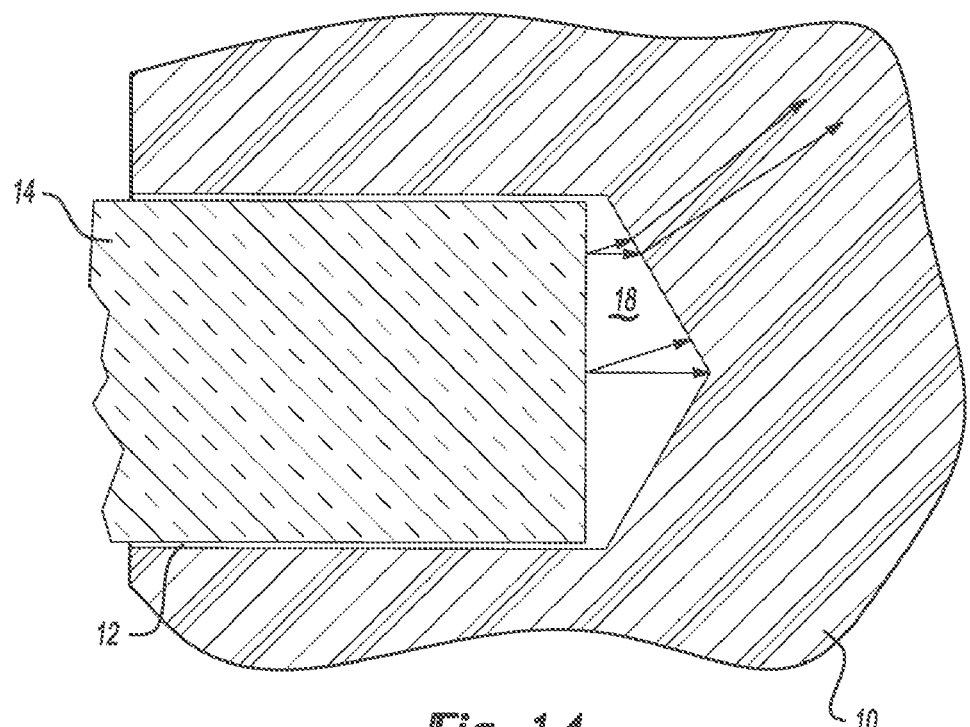
FIG. 14 is a side view of another exemplary embodiment of the light dispersing section of the pocket of the member of the device shown in FIG. 1.
Figure 15:
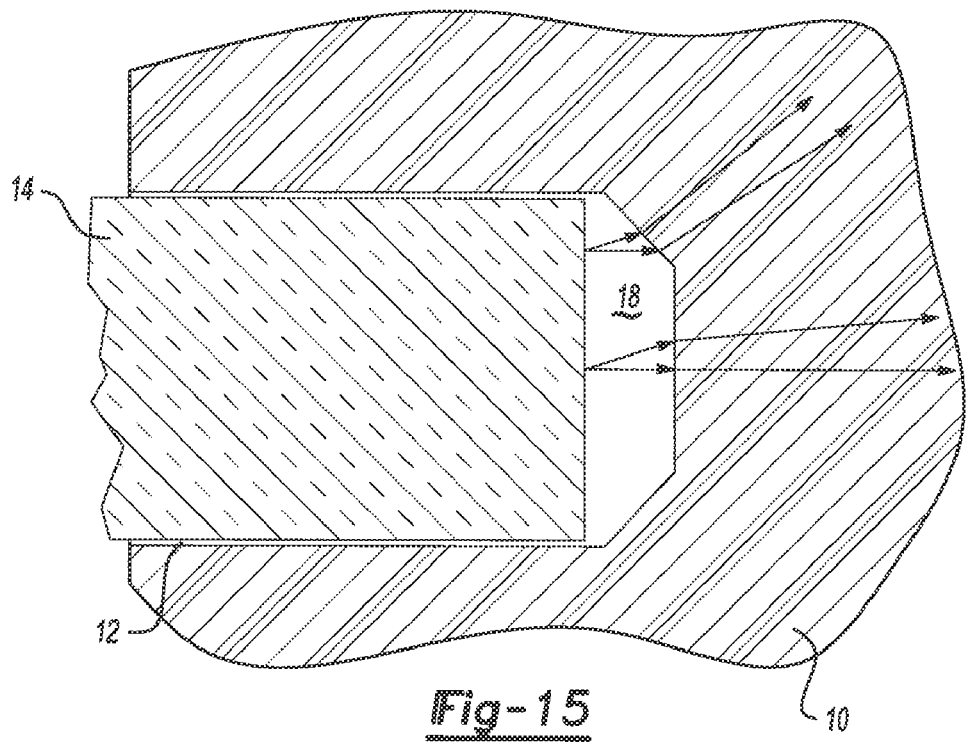
FIG. 15 is a side view of yet another exemplary embodiment of the light dispersing section of the pocket of the member of the device shown in FIG. 1.

Examples of the light dispersing section 18 with different geometries are shown in FIGS. 9-15. FIG. 9 has a pocket depth (defined as the distance between the waveguide distal end 16 and the pocket distal end 15) of about 0.01 mm, an initial radius of about 0.51 mm and a final radius of about 0.51 mm (i.e., the initial radius and the final radius are about the same). This geometry provides a flat shape as shown in FIG. 9. This geometry of the light dispersing section 18 provides little, if any, light redirection thereby allowing the illumination pattern to be determined by the waveguide 14 and other factors and/or elements within the member 10. FIG. 10 has a pocket depth of about 0.05 mm, an initial radius of about 0.51 mm and a final radius of about 0.4 mm (i.e., the initial radius is slightly larger than the final radius). This geometry provides a significantly truncated cone shape as shown in FIG. 10. FIG. 11 has a pocket depth of about 0.1 mm, an initial radius of about 0.2 mm and a final radius of about 0.0001 mm (i.e., the initial radius is much larger than the final radius). This geometry provides a small cone shape as shown in FIG. 11. FIG. 12 has a pocket depth of about 0.25 mm, an initial radius of about 0.25 mm and a final radius of about 0.0001 mm (i.e., the initial radius is much larger than the final radius). This geometry provides a small, full cone shape as shown in FIG. 12. FIG. 13 has a pocket depth of about 0.2mm, an initial radius of about 0.51 mm and a final radius of about 0.3 mm (i.e., the initial is larger than the final radius). This geometry provides a large truncated cone shape as shown in FIG. 13. FIG. 14 has a pocket depth of about 0.3 mm, an initial radius of about 0.51 mm and a final radius of about 0.001 mm (i.e., the initial radium is much larger than the final radius). This geometry provides a full cone shape as shown in FIG. 14. FIG. 15 has a pocket depth of about 0.2 mm, an initial radius of about 0.51 mm and a final radius of about 0.3 mm (i.e., the initial radius is larger than the final radius). This geometry provides a medium truncated cone shape as shown in FIG. 15.

As the geometry of the light dispersing section 18 changes (in this case, becoming more cone like in shape as shown in FIGS. 9-15), its corresponding illumination pattern of the device 100 also changes (in this case, providing higher intensity of light closer to the base portion 11 of the member 10). Higher intensity of light closer to the base portion 11 of the member 10 may provide for more illumination of a cavity's opening (e.g., the anterior nares, the opening of the ear cavity, etc.)

As discussed above, the present invention includes the manipulation of the geometry and/or the surface finish of the light dispersing section 18 in order to provide the desired and/or optimization illumination pattern for photodisinfection of a cavity. Depending upon the desired photodisinfection application in a cavity (e.g., the location of the microbes within the cavity), the geometry of the light dispersing section 18 can be adapted in various art-disclosed shapes (e.g., flat, concave or convex conic (including all variants from full to truncated), hemisphere with an apex cone, or a combination thereof) to provide the desired and/or optimized illumination pattern for photodisinfection of the cavity. Furthermore, the light dispersing section 18 and/or the pocket 12 can have a surface finish (e.g., smoothness, roughness, ribs, pigments, microspheres, Fresnel elements, deflective elements, reflective elements, facets, embossed patterns, or a combination thereof.) to provide the desired and/or optimized illumination pattern during photodisinfection.

Figure 16:
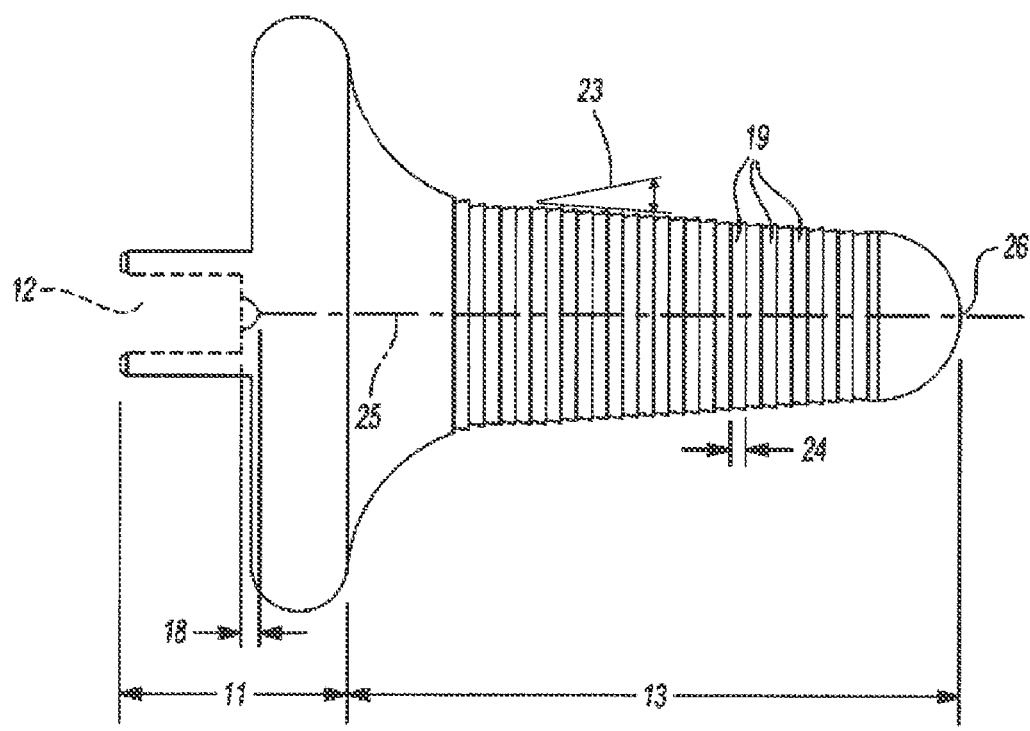
FIG. 16 is a sectional view of another exemplary embodiment of the device shown in FIG. 1.
Figure 17:
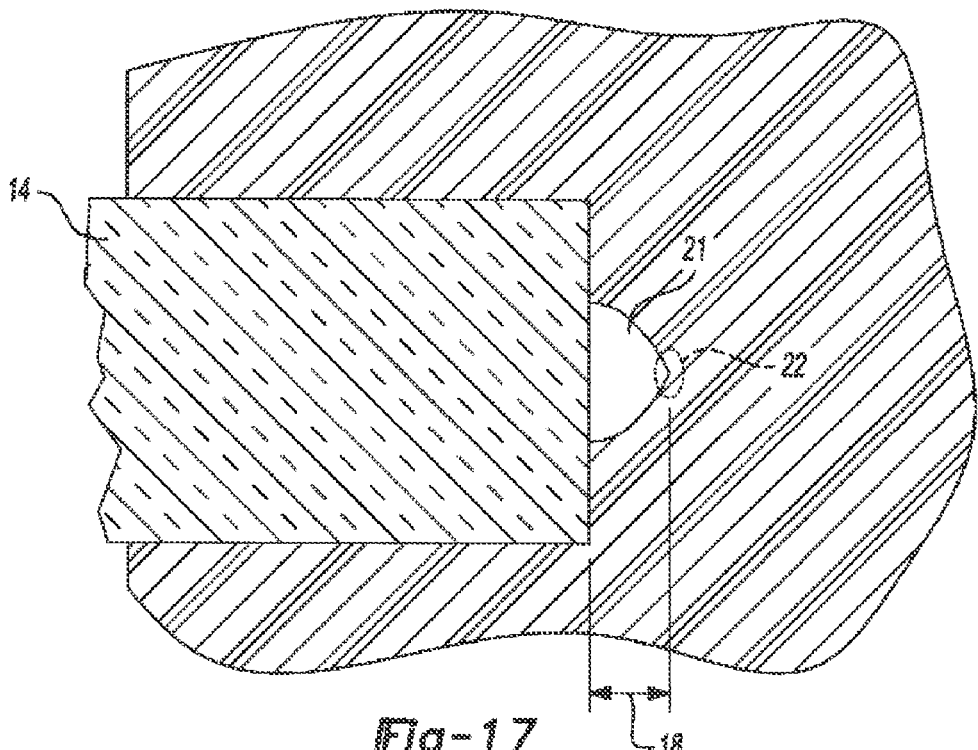
FIG. 17 is a side view of another exemplary embodiment of the light dispersing section of the pocket of the member of the device shown in FIG. 1.
Figure 18:
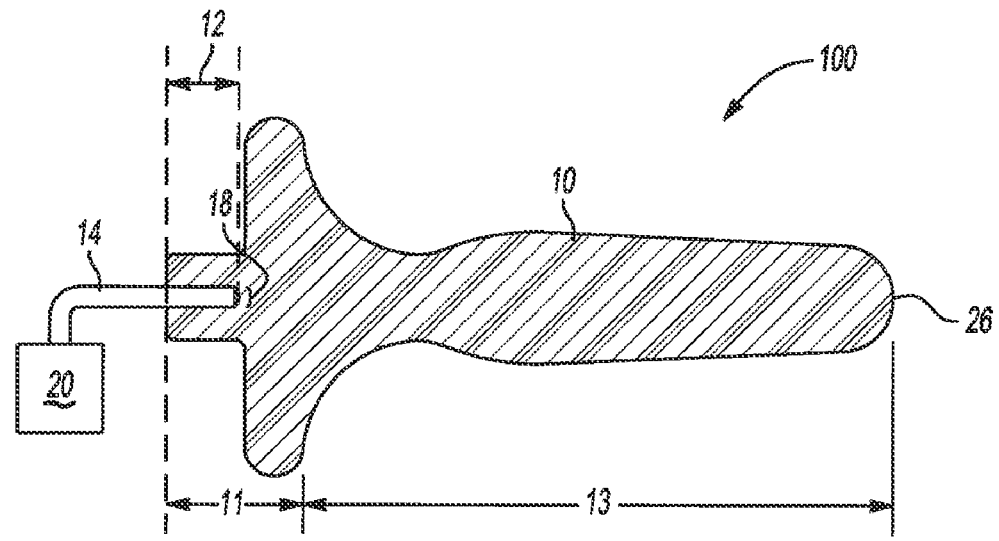
FIG. 18 is a sectional view of another exemplary device according to the present invention.

In FIG. 16, another embodiment of the device 100 is shown. In this embodiment, the insert portion 13 of the member 10 includes ribs 19 that assist in allowing illumination to be distributed uniformly down the length of the insert portion 13. The light dispersing section's geometry 18 includes a hemisphere 21 with an apex cone 22 which is shown in greater detail in FIG. 17. The hemisphere 21 helps gently spread light out of the waveguide 14 into slightly higher angles, facilitating illumination of the entire sidewall of the insert portion 13 instead of just its distal end 26. The apex cone 22 redirects the low angle light that would otherwise exclusively illuminate the distal end 26. The light is redirected into higher angles and illuminates the side wall of the inserted portion 13, increasing the amount of the light output in the treatment region. Treatment region is the area(s) of the member 10 where light output is desired. In one example, the hemisphere 21 is about 0.5 mm in radius. The apex cone 22 is about 0.175 mm in height and has a radius base of about 0.3 mm radius base. Each rib 19 of the insert portion 13 is constructed out of a wedge angle 23. In one embodiment, the wedge angle 23 is about 17 degree and rib width 24 ranges from about 0.48 mm to about 0.50 mm as shown in FIG. 18. In another embodiment, the wedge angle 23 is continuously variable and the average rays delivered from the light source 20 strike at normal incidence. Other examples of the wedge angle 23 have ranges from about 13 degree to about 33 degree and from about 15 degree to about 24 degree. Other examples of rib width are from about 1.5 mm to about 0.25 mm and from about 0.45 mm to about 0.55 mm.

The ribs 19 are rotated around the center line 25 of the member. The wedge angle 23 of each rib 19 is set so that the average ray that strikes the sidewall of the inserted portion 13 encounters a normal incidence output face and is emitted without significant refraction or redirection. The other face of each rib 19 is chosen to be parallel to the average ray angle so as to minimize the amount of internal scattering, maximizing the amount of light output in the treatment region. The ribs 19 provide another benefit in that, regardless of the refractive index of the media surrounding the member 10, the light is emitted in the desired pattern and in the treatment region.

The device 100 with the ribs 19 can provide more optimized illumination pattern for photodisinfection of the anterior nares as the light is distributed from the base portion 11 in a generally uniform fashion down the length of the inserted portion 13 as shown in the graph below. The graph below shows that difference in illumination pattern between the device 100 with ribs 19 (ribbed wall) and without ribs 19 (smooth wall). The graph set forth in Table 1 below demonstrates that the embodiment 120 with ribs 15 provides higher and more uniform illumination (relative optical) output for certain portion (e.g., from about 5 mm to 18 mm from the proximal end 25 of the insert portion 13.)

TABLE 1

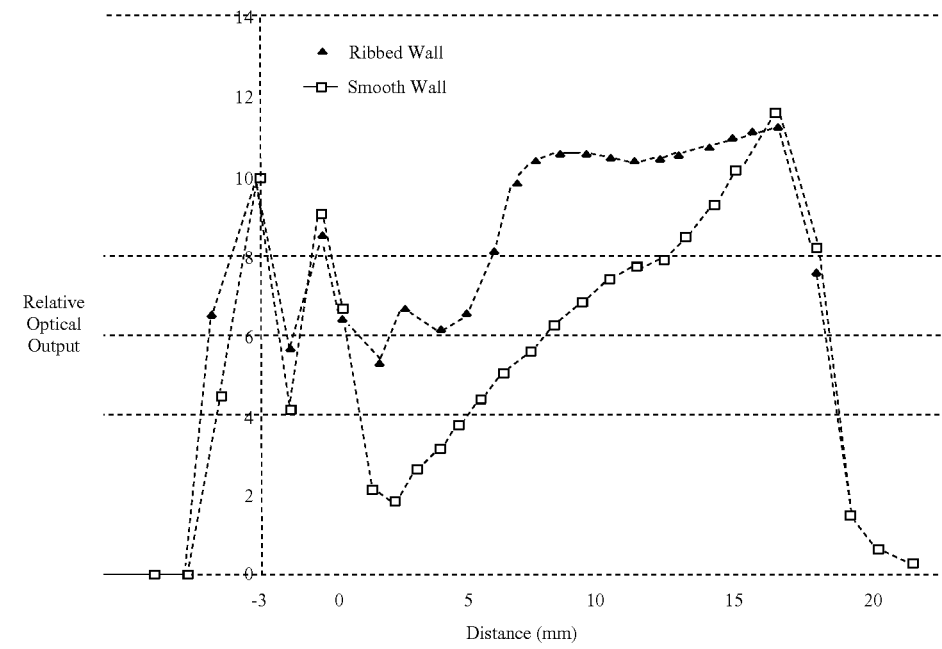

Referring back to FIG. 1, a light source 20 is connected to the waveguide 14 allowing transmission of light from the light source 20 via the waveguide 14 to the device 100. The light source 20 can be a separate unit or units in communication with the waveguide 14. Alternatively, the light source 20 can be directly embedded into the member 10. Generally, the light source 20 and the waveguide 14 are employed to deliver light of any desired wavelength(s) including visible and invisible light. For example, they can be employed for delivering light having wavelengths between and/or including deep UV to Far IR. In one embodiment, the light source 20 can provide a single wavelength at one time. In another embodiment, the light source 20 can provide two or more wavelengths at one time or sequentially.

FIG. 18 illustrates another embodiment of the device 100. The member 10 is constructed out of plastic and formed by art-disclosed injection molding process. The waveguide 14 is comprised of a low cost plastic optical fiber. The waveguide distal end 16 is located within the pocket 12 and the other end of the waveguide 14 is in communication with the light source 20. The waveguide distal end 16 (not shown in FIG. 18) has a flat and smooth surface. The base portion 11 of the member 10 is wider than the insert portion 13 and can optionally serve as a handle allowing easy handling. The base portion 11 also optionally serves as a stopper in that it stops insertion of the member 10 at a predetermined location. The base portion 11 can optionally reduce and/or prevent any photosensitizing composition from leaking out of the nasal cavity during photodisinfection. The insert portion 13 of the member 10 allows for deeper insertion of the device 100 into the nasal cavity while it eases such insertion with a smooth distal end 26. The insert portion 13 can focus the light coming out of it to be highly diverging, allowing the walls of the nasal cavity ahead of the insert portion 13 to be evenly illuminated. If desired, the distal end 26 can be optionally coated in order to reflect illumination back down the member 10. The light dispersing section 18 is a concave cone with an about 60 degree half angle and has a smooth surface. The surface finish and exterior shape of the member 10 and the surface finish and geometry of the waveguide distal end 16 and the light dispersing section 18 all work together to ensure illumination out of the waveguide 14 is deliver to most, if not all, surface areas of the nasal cavity including an optimized illumination pattern around the anterior nares.

It is contemplated that a photosensitizing composition is separately delivered rather than through the device 100. For example, a syringe or a tube and pump assembly may be employed to deliver the photosensitizing composition. Applying the photosensitizing composition to treatment site may be accomplished by any art-disclosed suitable technique. To a certain extent, the application technique will depend on the viscosity of the photosensitizing composition. Liquid compositions with relatively low viscosities may be sprayed into place, while higher viscosities liquids, solids and/or pastes may be brushed, dabbed or swabbed into place. Dry films of the composition may be manually placed in the treatment site.

When coupled with the light source 20 and the waveguide 14, the light delivered by the device 100 into the nasal cavity will illuminate the photosensitizing composition 28 residing on the surface areas of the cavity. This light delivered by the device 100 is in a wavelength range to activate the photosensitizing composition 28 so as to disinfect, inhibit, eliminate and/or kill the microbes in the cavity.

Figure 19:
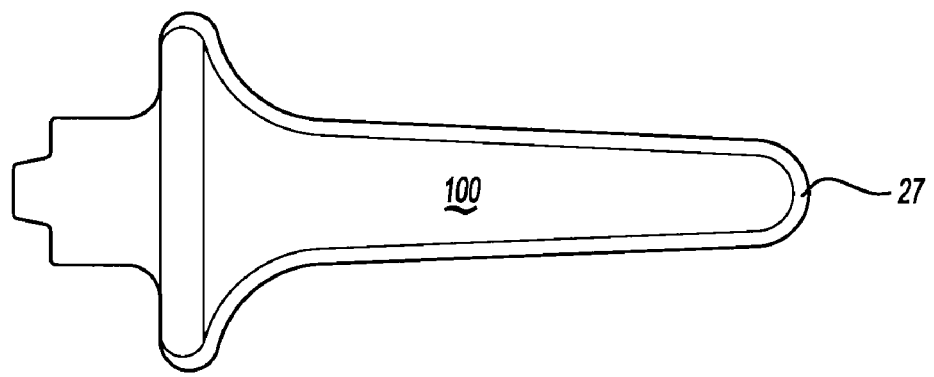
FIG. 19 is a side view of the device shown in FIG. 1 with an exemplary hermetic cap.

Depending on the material chosen to construct the device 100, the device 100 can be disposable, reusable and/or autoclavable. The device 100 can be packaged in a sterile environment. For example, the device 100 can be sealed with a hermetic cap 27 as illustrated in FIG. 19.

Figure 20:
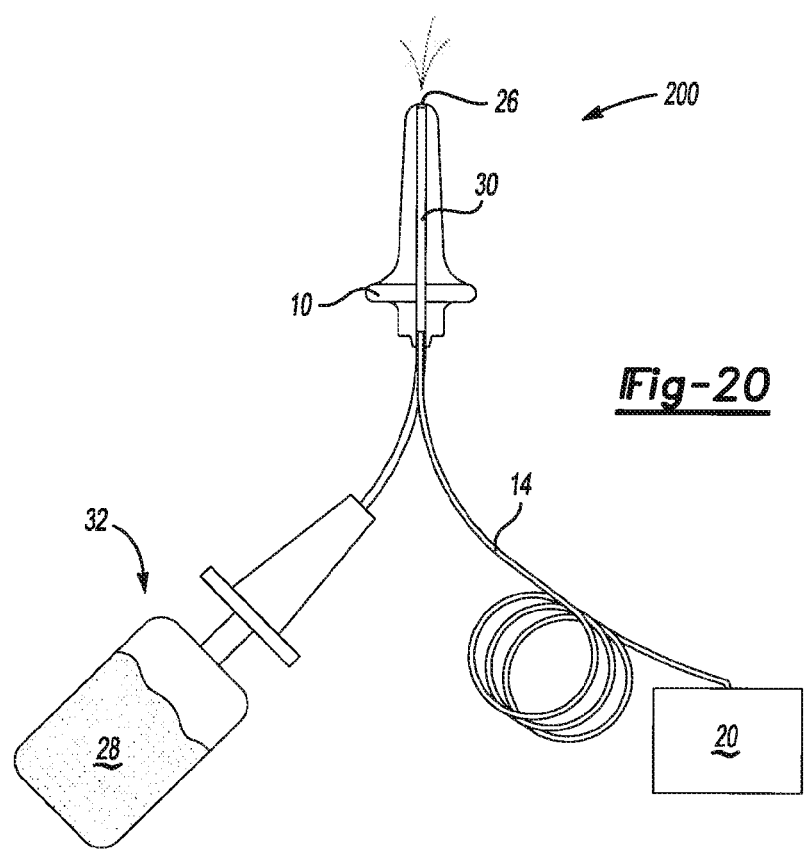
FIG. 20 is a sectional view of another exemplary device according to the present invention.

FIG. 20 illustrates another exemplary device 200 of the present invention which incorporates delivery of the photosensitizing composition 28. As the skilled artisan will recognize, the members and components have similarities in structure and use as compared to previous embodiments. As such, only differences are typically discussed, however, previous descriptions of similar or same components and uses thereof apply to the following embodiments as well. Device 200 includes all of the components discussed above for the device 100 (e.g., 10, 12, 20, etc.). The member 10 in device 200 further includes at least one tubular member 30 configured for fluid delivery of the photosensitizing composition 28. The tubular member 30 is in fluid communication with a fluid source 32 containing the photosensitizing composition 30. In this illustrated example, the fluid source 32 is shown as a pump. When the fluid source 32 is activated, the photosensitizing composition 30 will travel through the tubular member 30 to opening at the member distal end 26 emit into the nasal cavity. If desired, the opening of the member distal end 26 can optionally include an atomizing (e.g., spraying or the like) nozzle.

Figure 21:
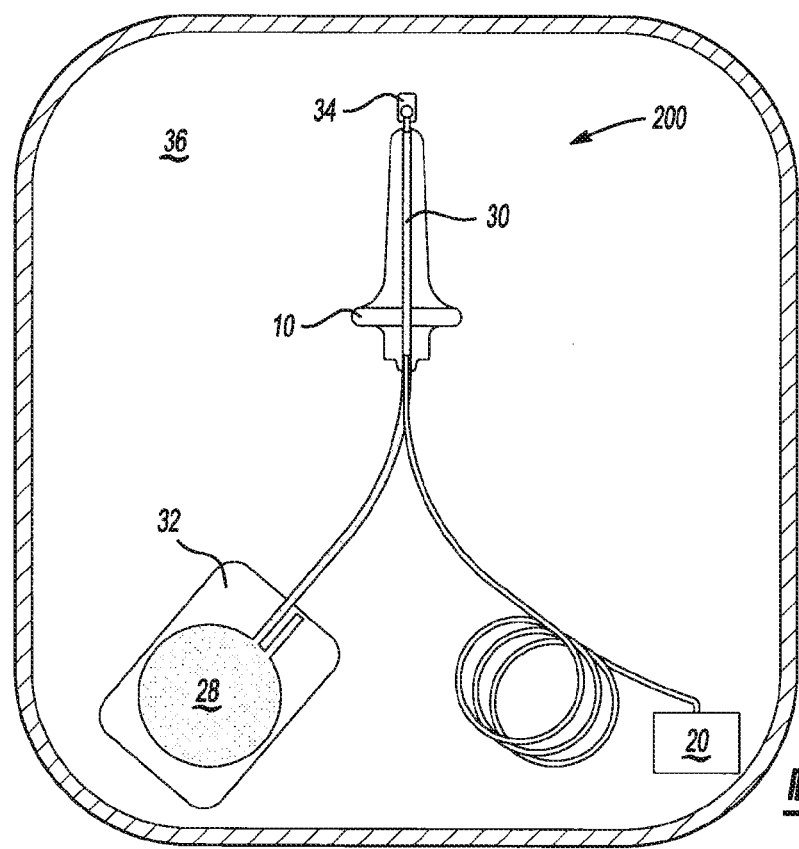
FIG. 21 is a sectional view of yet another exemplary device according to the present invention.

FIG. 21 illustrates an alternative embodiment of device 200. This embodiment is basically the same as the device 200 shown in FIG. 20 except that the fluid source 32 is a squeeze blub and the opening or port 38 of the tubular member at the member distal end 26 is sealed with an optional removable (e.g., twist off/snap off) tip 34. The device 200 can optionally be packaged in a sterile package 36 and made available as a disposable device as illustrated in FIG. 21.

Figure 22:
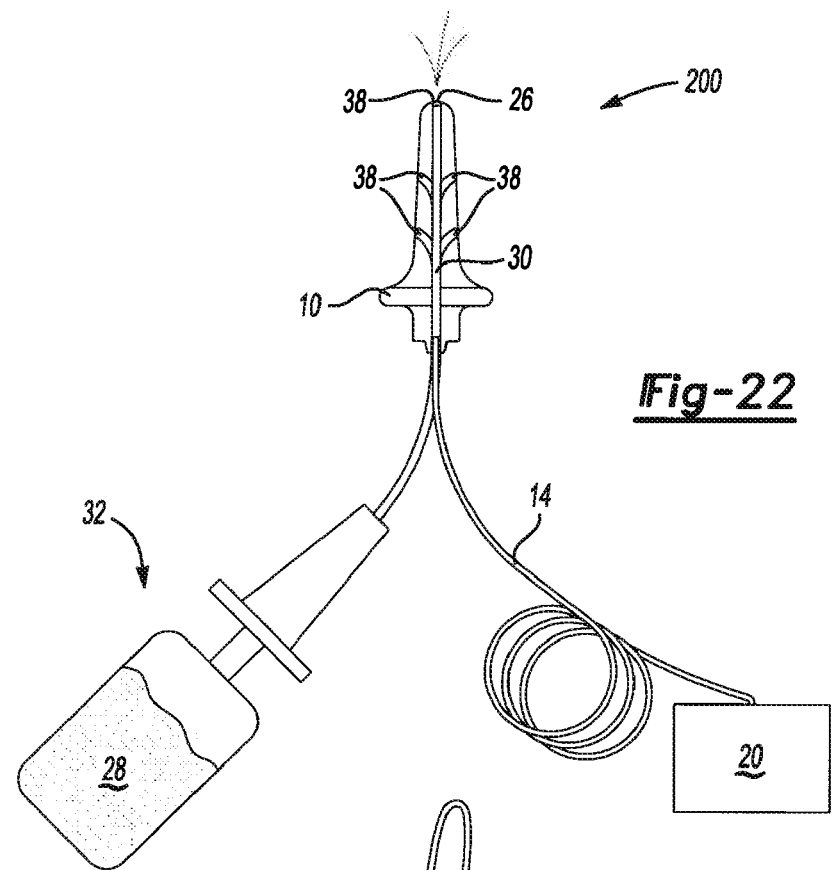
FIG. 22 is a sectional view of another exemplary device according to the present invention.

FIG. 22 illustrates another alternative embodiment of device 200. This embodiment is basically the same as the device 200 shown in FIG. 21 except that the tubular member 30 has multiple branches allowing multiple ports 38 to dispense the photosensitizing composition 28. If desired, any one of the multiple ports 38 can optionally include an atomizing nozzle.

Figure 23:
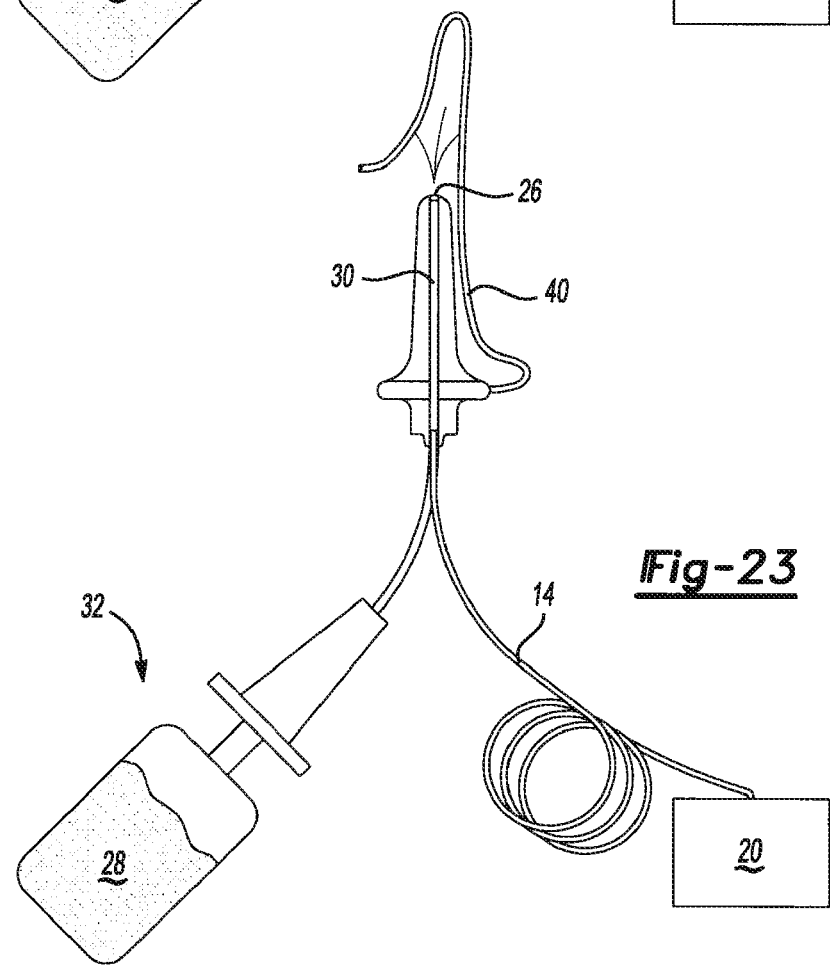
FIG. 23 is a sectional view of yet another exemplary device according to the present invention.

FIG. 23 illustrates another alternative embodiment of device 200. This embodiment is basically the same as the device shown in FIG. 21 except that it includes a retention feature 40 to assist in securing the device 200 in place during treatment. The retention feature 40 may be part of the member 10 or attached to the member 10 (e.g. a soft wire spring clamp). The retention feature 40 may have any number of ergonomic shapes that hold against the cavity without causing discomfort. Alternatively, the retention feature 40 may be a simple adhesive strip included in the treatment kit.

Figure 24:
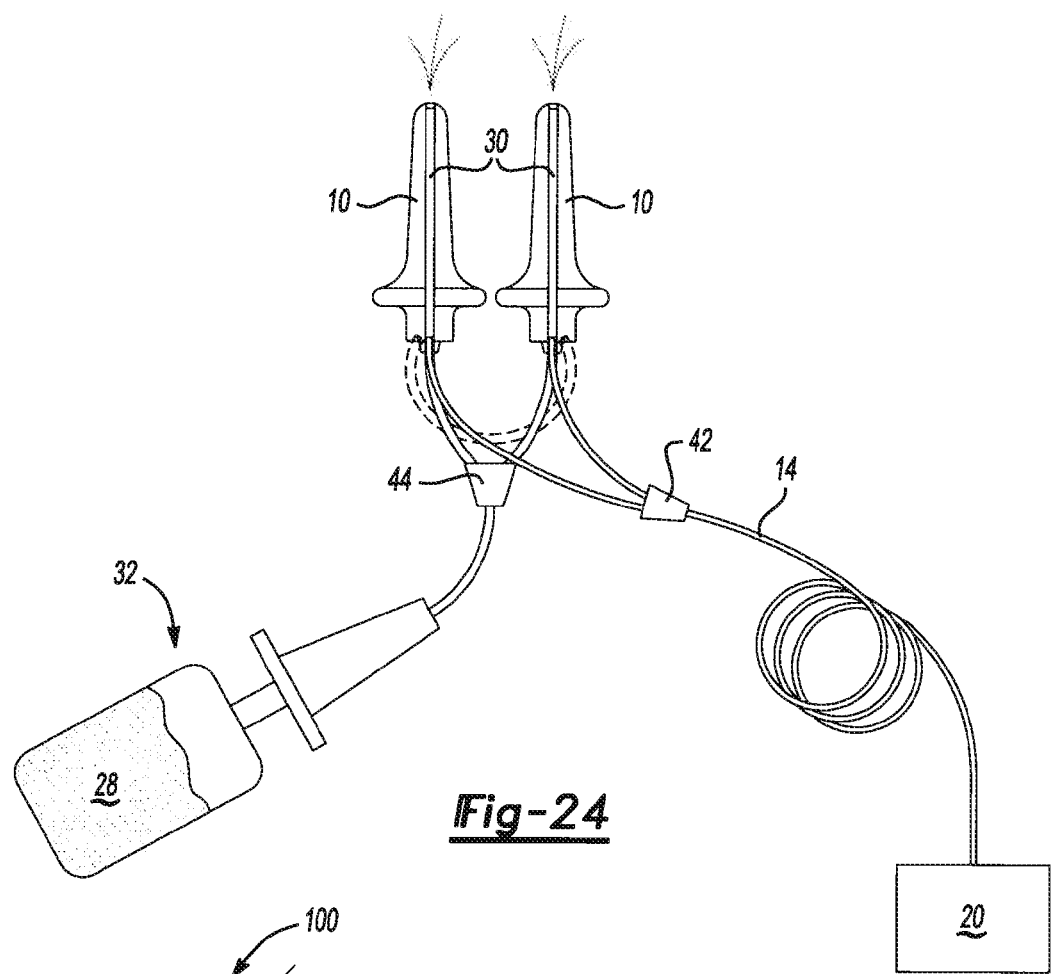
FIG. 24 is a sectional view of another exemplary device according to the present invention.

FIG. 24 illustrates another alternative embodiment of device 200. This embodiment is basically the same as the device 200 shown in FIG. 21 except that it allows both nostrils to be treated simultaneously with an additional member having basically the same structural component as the member 10. An alternative embodiment includes the device 100 discussed above except that it allows both nostrils to be treated simultaneously with an additional member having the same structural component as the member 10. It is optionally that the additional member and the member 10 may be attached to each other via art-disclosed attachment means. The embodiment shown in FIG. 24 has a light distribution manifold 42 to take a single input waveguide 14 and route the light to multiple members 10. Alternatively, multiple source waveguides 14 and/or multiple light sources 20 can be used.

The fluid source 32 shown in FIG. 24 is a single pump attached to both members 10 of device via a fluid distribution manifold 44. Alternatively, multiple pumps can be used as the fluid source 32. The two members 10 shown in FIG. 24 are connected only by their shared waveguide 14 and tubular members 30. Alternatively, an additional structural member can used to hold the two members 10 in position relative to each other. This structural member can also be formed with a slight inward bias so that when the two members 10 are inserted to provide a slight inward spring force in order to help "clamp" the members 10 in place during treatment.

B. Device for Photodisinfection of Other Cavities

As discussed above, depending on the desired application of photodisinfection, the geometry and surface finish of the member 10 including the pocket 12 can be modified and/or adapted to change the ergonomics and/or the illumination pattern (e.g., the light distribution or the like). For example, the device 100 and/or the device 200 shown above can be made smaller to provide an ergonomic fit within body cavities such as ear, vagina, lung, the entire digestive track (e.g., throat, esophagus, stomach, intestines, rectum, or the like) and any open wound cavity. For example, an exemplary embodiment of the device 100 (see FIG. 25) with the member 10 is designed to fit not only within the nasal cavity (see FIG.

Figure 25:
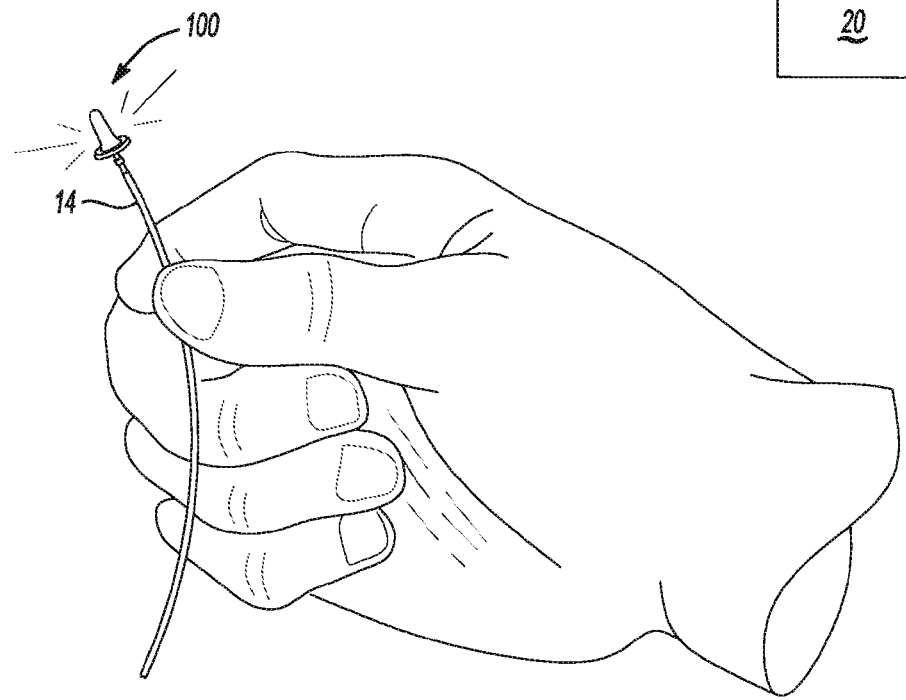
FIG. 25 is a drawing of an exemplary device according to the present invention illuminated by its waveguide held in a human hand.
Figure 26:
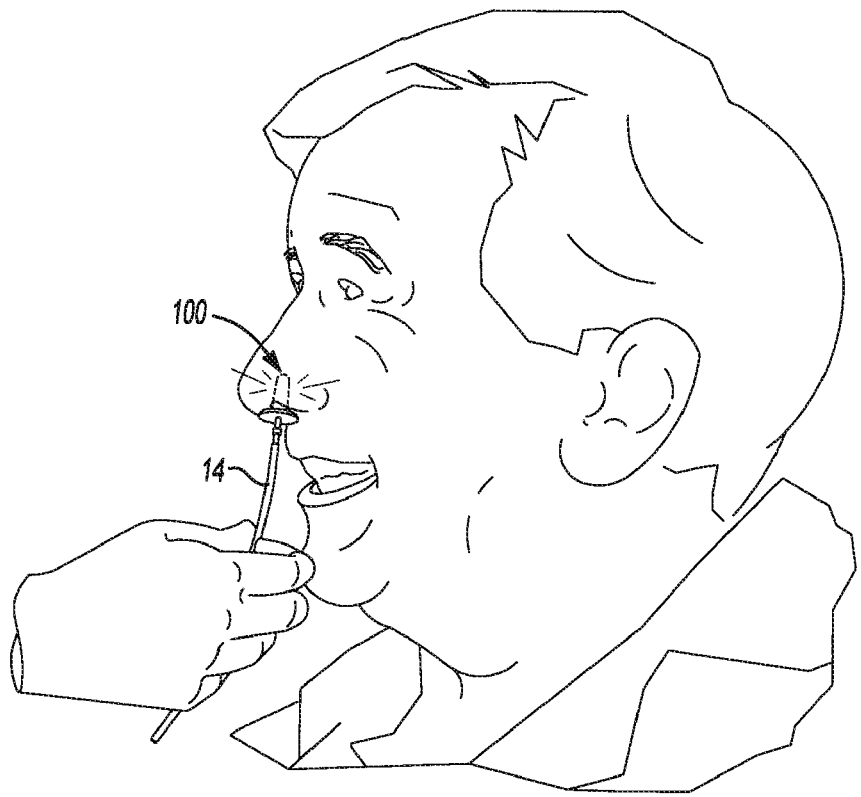
FIG. 26 is a drawing of the device shown in FIG. 25 placed in a patient's nasal cavity.
Figure 27:
FIG. 27 is a drawing of the device shown in FIG. 25 placed in a patient's ear cavity.

26) but also for the ear cavity (see FIG. 27). FIGS. 25-27 are shown with illumination from the waveguide 14. In another example, the device 100 and/or the device 200 shown above can be made even smaller to allow entry into body cavities that may have restricted entry or opening such as gall bladder, bladder, or the like. It can be appreciated that one skilled in the art can use the present invention in numerous other applications not expressly listed in this paragraph to reduce and/or eliminate microbes in a cavity.

Unless stated otherwise, dimensions and geometries of the various structures depicted herein are not intended to be restrictive of the invention, and other dimensions or geometries are possible. Plural structural components can be provided by a single integrated structure. Alternatively, a single integrated structure might be divided into separate plural components. In addition, while a feature of the present invention may have been described in the context of only one of the illustrated embodiments, such feature may be combined with one or more other features of other embodiments, for any given application. It will also be appreciated from the above that the fabrication of the unique structures herein and the operation thereof also constitute methods in accordance with the present invention. It is preferred that the components of the treatment kit are placed in sterile package(s).

III. Kit and System

The present invention includes a treatment kit for photodisinfection of a body cavity including the device (100 or 200 as described above), the photosensitizing composition 28 contained in the fluid source 32. The treatment kit may optionally include the waveguide 14. Examples of the treatment kit are shown in FIGS. 20-24. The fluid source 32 can be a syringe, a squeeze blub, or a tube and pump assembly. The fluid source 32 may optionally further includes an application tip. The application tip is coupled to the syringe, a squeeze blub, or a tube and pump to deliver the photosensitizing composition 28 into the body cavity. The application tip can be any art-disclosed application tip. Examples of such application tip include self-saturating swabs (without and without custom filled—Product Numbers 4545 and 4620) manufactured by Puritan® Medical Products LLC Company located in Guilford, Me. See www.puritanmedproducts.com.

Figure 28:
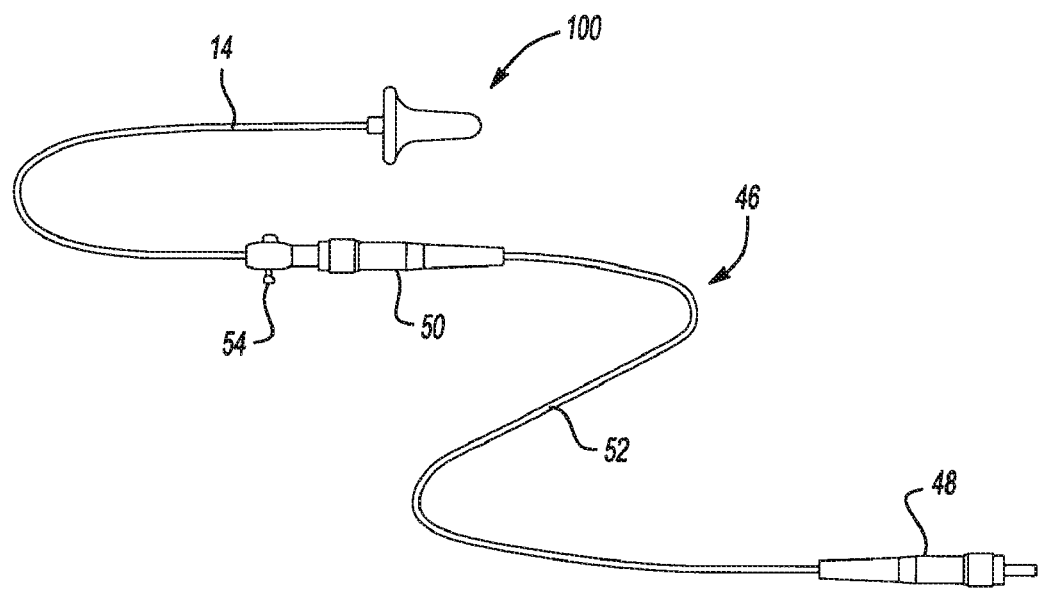
FIG. 28 is a side view of the device shown in FIG. 1 with a connector for a light source.
Figures 29, 30:
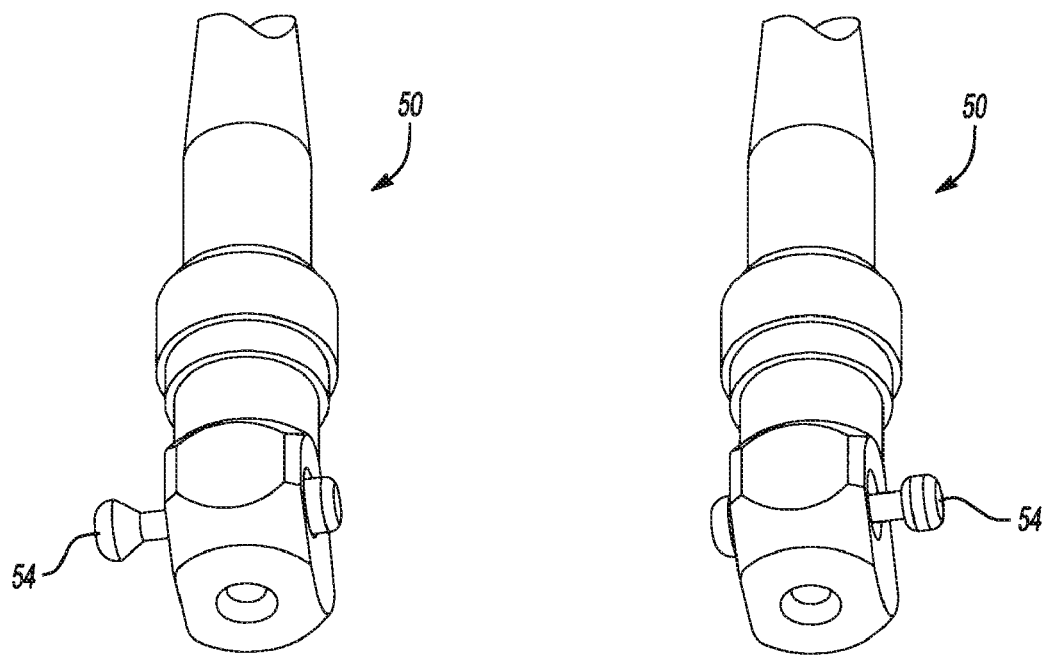
FIG. 29 is a more detail view of a waveguide adapter of the connector shown in FIG. 28.
FIG. 30 is another more detail view of a waveguide adapter of the connector shown in FIG. 28.

It is preferred that most, if not all, of the components of the treatment kit are suitable for single use (i.e., constructed of disposable materials). For example and as shown in FIGS. 20-24, the device can be constructed of disposable material and a disposable optical fiber can serve as the waveguide 14. Referring to FIG. 28, the waveguide 14 can be connected to the light source 20 (not shown in FIG. 28) via a connector 46. The connector 46 includes a light source adapter 48 that connects to the light source 20. The connector 46 further includes a waveguide adapter 50 designed to be removably attached to the waveguide 14. The connector 46 may optionally include communication means 52 (e.g., cable or the like) between the light source adapter 48 and the waveguide adapter 50 as shown in FIG. 25. As shown in FIGS. 29-30, the waveguide adapter 50 includes removable means 54 allowing the waveguide 14 to be removably attached.

Figure 31:
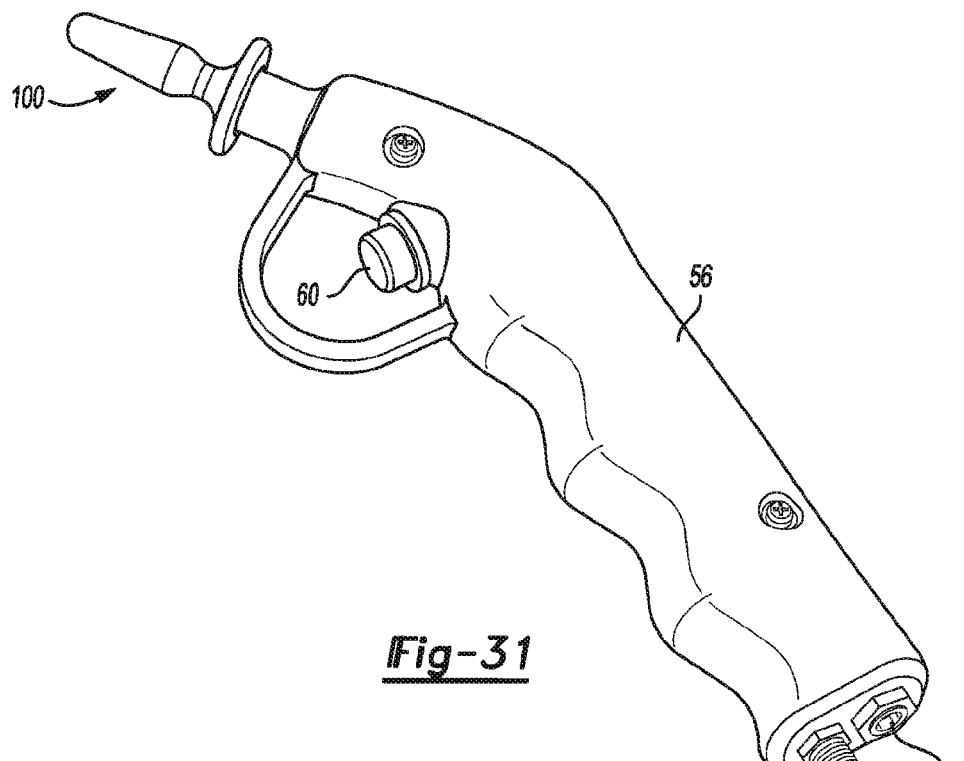
FIG. 31 is a side view of an exemplary device according to the present invention with an exemplary holder.
Figure 32:
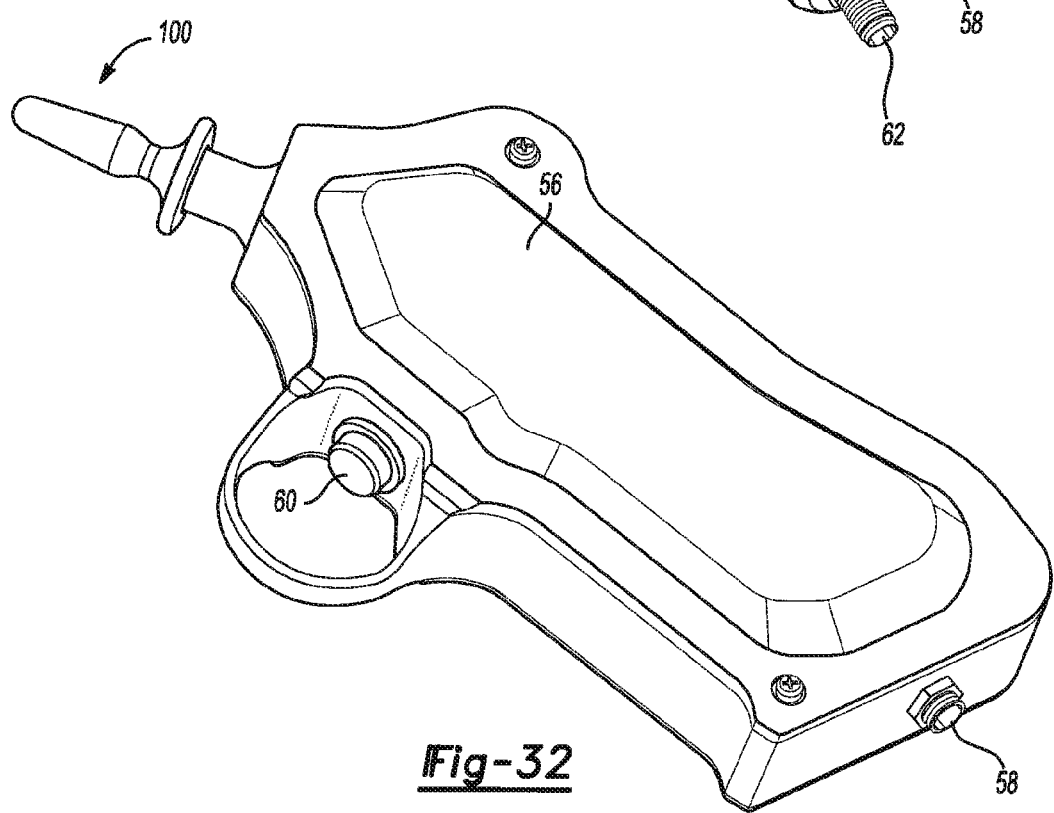
FIG. 32 is a side view of another exemplary device according to the present invention with another exemplary holder.

In another embodiment of the present invention and referring to FIGS. 31-32, the waveguide 14 is incorporated into a holder 56. The device (100 or 200) is connected to the waveguide 14 within the holder 56. The holder 56 may optionally includes: (1) a communication port 58 for light communication between the waveguide 14 and the light source 20 via a fiber optic cable (not shown in FIGS. 32-33); (2) a switch 60 for controlling the light input into the device; and/or a fluid communication means 62 (shown in FIG. 32) for fluid communication between the device and the fluid source 32.

The present invention includes a treatment system for photodisinfection of a cavity comprising the device of the present invention (100 or 200 described above), the waveguide 14 and the light source 20. The light source 20 may optionally include a foot switch for turning the light source 20 on and/or off. The light source 20 may also optionally include a separate power supply. The treatment system may optionally further include one or more of the following components: the connector 46, the holder 56, safety glasses, the photosensitizing composition 28, the fluid source 32 (with or without the application tip) or the like.

When used for disinfection of a body cavity, it is preferred that the device (100 or 200) and/or any components of the treatment kit and the treatment system described above that may come into contact with the body be constructed of biocompatible materials.

IV. Applications

A. Method for Photodisinfection of a Cavity

The present invention includes a method for photodisinfection of a cavity comprising applying a photosensitizing composition to treatment site within the cavity. The method further includes inserting the device 100 described above into the cavity and applying light delivered by the device 100 to the treatment site at a wavelength absorbed by the photosensitizing composition so as to inhibit or eliminate microbes located in the treatment site.

The present invention further includes a method for photodisinfection of a cavity comprising inserting the device 200 described above into the cavity and applying a photosensitizing composition and light to the treatment site wherein both the photosensitizing composition and light are both delivered by the device 200 to the treatment site and the light is at a wavelength absorbed by the photosensitizing composition so as to inhibit or eliminate microbes located in the treatment site. When the present invention is in use, the fluid source delivers the photosensitizing composition to the device 200, which is configured for dispensing light in a desired illumination pattern to the treatment area. The method can be performed by (1) applying the photosensitizing composition first and then the light; or (2) applying the photosensitizing composition and the light simultaneously. Depending on the nature and extent of the microbes located at the treatment site, the practitioner may apply multiple cycles of light applications (e.g., about 2 to about 10, about 3 to about 5, etc.) to the treatment site or the entire method can be repeated multiple times (e.g., about 2 to about 10, about 3 to about 5, etc.) until the desired effects have been reached.

As discussed above, the light required for these methods is delivered to the device (100 or 200) by the light source 20 via the waveguide 14 described above. When used for photodisinfection of a body cavity, it is preferred that the application of light does not cause physiological damage to host tissue at and surrounding the treatment site.

B. Treatment of MRSA, *E. coli* and *E. fecalis*

MRSA, a spherical Gram-positive aerobe, accounts for up to 50% of nosocomial *S. aureus* infections, and represents a multi-billion dollar problem in critical care units, intensive care units and general hospitals worldwide. Because bacteria naturally adapt to antibiotics, more than 95% of patients with MRSA do not respond to first-line antibiotics. Certain MRSA strains are now even resistant to glycopeptide antibiotics like Vancomycin®, removing the last remaining effective antibiotic treatment for the disease. Due to the fact that MRSA is resistant to most antibiotics such as methicillin, oxacillin, penicillin and amoxicillin, photodisinfection is a desirable alterative treatment method.

As Examples I-III below show, photodisinfection treatment using methods contemplated by the present invention is effective in killing MRSA and other microbes such as *E. coli, E. fecalis*, etc. The present invention includes methods to treat MRSA, *E. coil* and/or *E. fecalis* comprising of applying a photosensitizing composition comprising methylene blue to treatment site within the body cavity where MRSA, *E. coil* and/or *E. fecalis* organisms are located. It is preferred that the methylene blue concentration ranges from about 0.001 wt % to about 1 wt %, more preferably from about 0.01 wt % to about 0.5 wt %, even more preferably from about 0.02 wt % to 0.1 wt %, and most preferably at about 0.1 wt %. It is preferred that prior to the application of light, the photosensitizing composition is placed into contact with the treatment site for at least about 1 second, more preferably for at least about 5 seconds, even more preferably for at least about 10 seconds, and most preferably from about 10 seconds to 30 seconds.

The methods further include applying light to the treatment site at a wavelength ranges preferably from about 650 nm to 685 nm, more preferably from about 660 nm to about 680 nm, and most preferably at about 665 nm to about 675 nm. Depending on the methylene blue concentration and the power of the light source, the application of light to the treatment site may only require a short period of time such as from about 15 seconds to less than about 5 minutes, preferably from about 15 seconds to about two minutes, more preferably for about 15 seconds to about 90 seconds, and most preferably for about 30 seconds to 60 seconds. The light energy provided during each cycle of application of light is preferred to range from about 1 $J/cm^2$ to about 25 $J/cm^2$, more preferably at about 5 $J/cm^2$ to about 20 $J/cm^2$, and most preferably at about 6 $J/cm^2$ to about 12 $J/cm^2$. Depending on the nature and extent of the MRSA, *E. coli* and/or *E. fecalis* located at the treatment site, the practitioner may apply multiple cycles of light applications (e.g., about 2 to about 10, about 3 to about 5, etc.) to the treatment site thereby resulting in a total accumulated light energy applied to treatment site that can be substantially higher than the light energy provided during each cycle. Again depending on the nature and extent of the microbes located at the treatment site, the entire method can be repeated multiple times (e.g., about 2 to about 10, about 3 to about 5, etc.) until the desired effects have been reached. It is preferred that the selections of methylene blue concentration, wavelength, and/or total accumulated light energy applied to treatment site will allow the methods of the present invention to kill over about 90%, more preferably over 95%, and most preferably over 99% of the target microbes at the treatment site. It is also preferred that the application of light to the treatment site does not cause physiological damage to the host tissues at and/or surround the treatment site.

The application of light can be delivered by the device (100 or 200) and the treatment system of the present invention, the optical probe disclosed in commonly owned PCT Patent Publication No. WO2006115761, the Periowave™ laser light system manufactured by Ondine Biopharma Corporation located in Vancouver, Canada (see www.ondinebiopharm.com), and any other art-disclosed suitable light delivery devices and/or systems. WO2006115761 is hereby incorporated by reference in its entirety for all purposes.

C. Method for Nasal Decolonization of Microbes

The nasal cavity can be an active site for microbes and many colonies of microbes reside at the anterior nares. MRSA is an example of such microbes. Illumination of the anterior nares enables photodisinfection of MRSA and other microbes. The present invention can be used to curb the spread of MRSA and other microbes.

The present invention includes a method for nasal decolonization of microbes comprising applying a photosensitizing composition to anterior nares of a nasal cavity. The method further includes inserting the device 100 into the nasal cavity and applying light to the anterior nares via the device 100 at a wavelength absorbed by the photosensitizing composition so as to inhibit or eliminate microbes located in the anterior nares.

The present invention further includes a method for nasal decolonization of microbes comprising inserting the device 200 described above into the nasal cavity and applying a photosensitizing composition and light to the anterior nares wherein both the photosensitizing composition and light are both delivered by the device 200 to the anterior nares and the light is at a wavelength absorbed by the photosensitizing composition so as to inhibit or eliminate microbes located in the anterior nares. The method can be performed by (1) applying the photosensitizing composition first and then the light; or (2) applying the photosensitizing composition and the light simultaneously.

Optionally, these methods may include allowing the photosensitizing composition is placed into contact with the anterior nares for at least about 1 second, more preferably for at least about 5 seconds, even more preferably for at least about 10 seconds, and most preferably from about 10 seconds to 30 seconds, prior to the application of light.

Depending on concentration of photosensitizer(s) contained in the photosensitizing composition. and the power of the light source, the application of light to the anterior nares may only require a short period of time such as from about 15 seconds to less than about 5 minutes, preferably from about 15 seconds to about two minutes, more preferably for about 30 seconds to about 90 seconds, and most preferably for about 30 seconds to 60 seconds. The light energy provided during each cycle of application of light is preferred to range from about 1 $J/cm^2$ to about 25 $J/cm^2$, more preferably at about 5 $J/cm^2$ to about 20 $J/cm^2$, and most preferably at about 6 $J/cm^2$ to about 12 $J/cm^2$. Depending on the nature and extent of the microbes located at the anterior nares, the practitioner may apply multiple cycles of light applications (e.g., about 2 to about 10, about 3 to about 5, etc.) to the anterior nares thereby resulting in a total accumulated light energy applied to treatment site that can be substantially higher than the light energy provided during each cycle. Again depending on the nature and extent of the microbes located at the treatment site, the entire method can be repeated multiple times (e.g., about 2 to about 10, about 3 to about 5, etc.) until the desired effects have been reached. It is preferred that the selections of photosensitizer concentration, wavelength, and/or total accumulated light energy applied to treatment site will allow the methods of the present invention to kill over about 90%, more preferably over 95%, and most preferably over 99% of the target microbes at the anterior nares. It is preferred that the application of light to the anterior nares does not cause physiological damage to the host tissues at and/or surround the anterior nares or the nasal cavity.

As discussed above, the desired illumination pattern delivered by the device (100 or 200) for photodisinfection of the nasal cavity is provided by at least one of the elements selected from the group consisting of: surface finish of the light dispersing section 18, geometry of the light dispersing section 18, surface finish of the member's 10 exterior surface, geometry of the member 10 and a combination thereof. Also, the light required for these methods is delivered to the device (100 or 200) by the light source 20 via the waveguide 14. As noted above, the surface finish and/or geometry of the distal end 16 of the waveguide 16 may also assist in providing the desired illumination pattern.

The application of light can be delivered by the device (100 or 200) and the treatment system of the present invention, the optical probe disclosed in commonly owned PCT Patent Publication No. WO2006115761, the Periowave™ laser light system manufactured by Ondine Biopharma Corporation located in Vancouver, Canada (see www.ondinebiopharm.com), and any other art-disclosed suitable light delivery devices and/or systems. WO2006115761 is hereby incorporated by reference in its entirety for all purposes.

The methods for nasal decolonization of microbes can be applied to a single nasal cavity or to both nasal cavities in a serial or parallel (e.g., simultaneously) fashion D. Treatment for Otitis Externa Otitis externa, also known as swimmer's ear, is an inflammatory process of the external auditory canal. Otitis externa causes inflammation of the external auditory meatus, generally characterized by discharge, itching and local discomfort. Otitis externa may decrease the protective barrier of wax in the ear resulting to cracks in the waterlogged skin.

Otitis externa is most commonly caused by microbial infection (usually bacterial and/or fungal). The external auditory canal has a normal bacterial flora and remains free of infection unless its defenses are disrupted. When disruption occurs, a new pathogenic flora develops that is dominated usually by *Pseudomonas aeruginosa* and *Staphylococcus aureus* (and MRSA). *Aspergillus* and *Candida* are the most common fungi causing otitis externa. Excessive moisture (e.g., swimming, perspiration, high humidity, etc.), trauma to the external auditory canal, and insertion of foreign objects into the external auditory canal (e.g., hearing aids, cotton swabs, fingernails, ear plugs, etc.) impair the external auditory canal's natural defenses and are common precipitants of otitis externa. If otitis externa is not optimally treated, especially in immunocompromised patients, the potentially life-threatening infection can spread to the surrounding tissues (e.g., mastoid or temporal bone).

Conventional treatment for otitis externa generally involves the use of topical antibiotics and/or antifungal along with acid (usually in a fluid form such as ear drops). Steroids may also be added to decrease the inflammation and edema of the external auditory canal and resolve symptoms more quickly. Oral antibiotics may also be given, usually in situations where the otitis externa is persistent. Treatment recommendations vary somewhat, but it is most commonly recommended that the topical medications be given for three days beyond the cessation of symptoms (typically five to seven days); however, in patients with more severe infections, 10 to 14 days of treatment may be required. Unfortunately, during the recovery period, the patient is very susceptible to re-infection and chronic otitis externa may occur.

Sensitization to the topical antibiotics may occur. In the 1970s, topical sensitization to was detectable in about 8% of individuals with chronic otitis externa. In the 1980s, this incidence doubled to 16%, and in the 1990s, the incidence doubled again to 30-35%. The incidence of cutaneous sensitization has apparently doubled each decade for the last 3 decades, presumably as a result of widespread exposure to neomycin-containing drops. See Billings, Kathleen R. (Mar. 21, 2006) Ototopical Antibiotics, http://www.emedicine.com/ent/topic362.htm.

Figure 37:
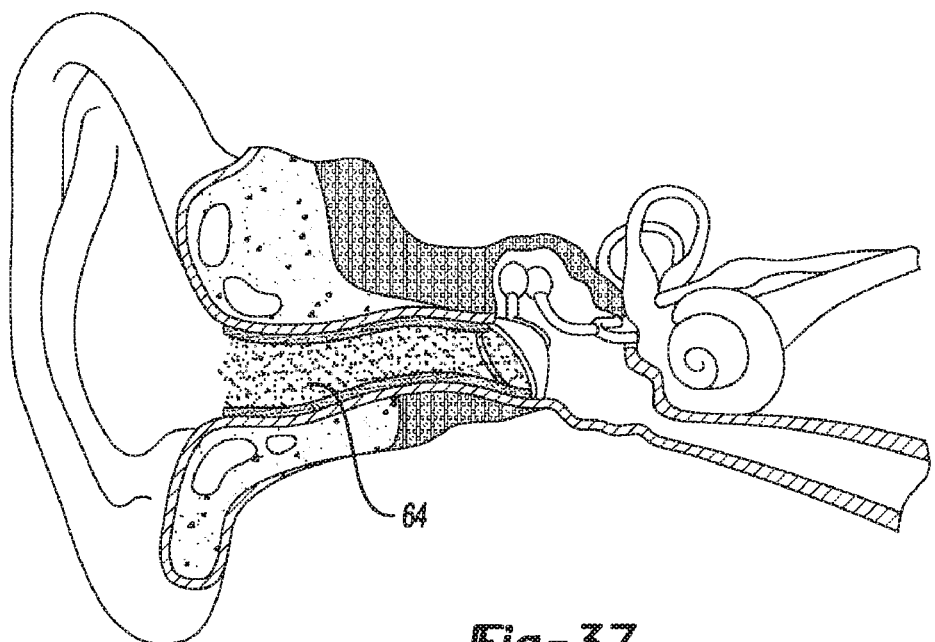
FIG. 37 is a cross-section drawing of a human's ear and external auditory canal with otitis externa showing a photosensitizing composition in the treatment site in accordance to the principles of the present invention.

The present invention provides a method to treat otitis externa by first applying a photosensitizing composition to treatment site within ear cavity. Referring to FIG. 37, the treatment site 64 within the ear cavity is defined herein as the area where otitis externa is located, usually in outer ear and external auditory canal but may also include the tympanic membrane.

In one embodiment, the photosensitizing composition includes methylene blue. See e.g., Examples IV to VI below. In another embodiment, the photosensitizing composition includes toluidine blue. See Example VII below. It is preferred that either the concentration of methylene blue and/or the toluidine blue ranges from about 0.001 wt % to about 1 wt %, more preferably from about 0.01 wt % to about 0.5 wt %, even more preferably from about 0.02 wt % to 0.1 wt %, and most preferably at about 0.1 wt %.

Figure 38:
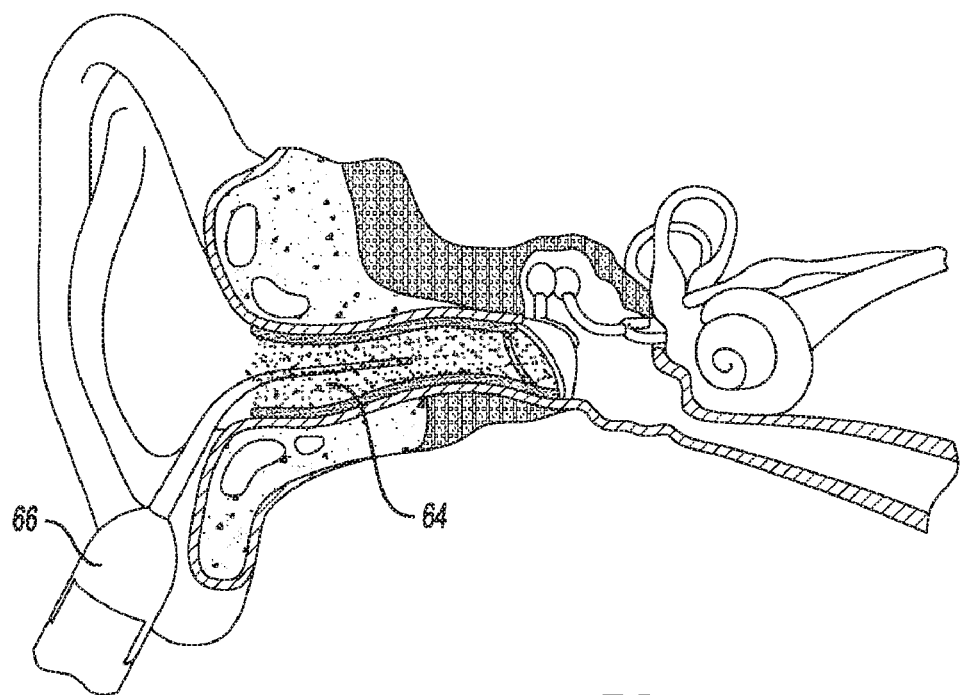
FIG. 38 is the same drawing as FIG. 37 but with the addition of an exemplary photodisinfection device in accordance to the principles of the present invention.
Figure 39:
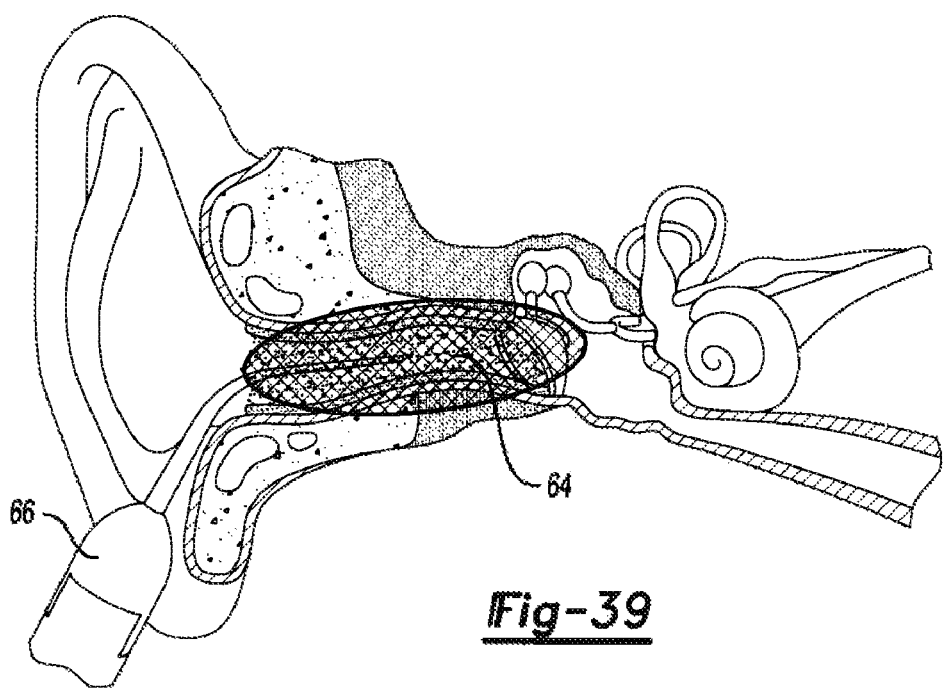
FIG. 39 is the same drawing as FIG. 37 but with the addition of light energy delivered by the photodisinfection device.
Figure 41:
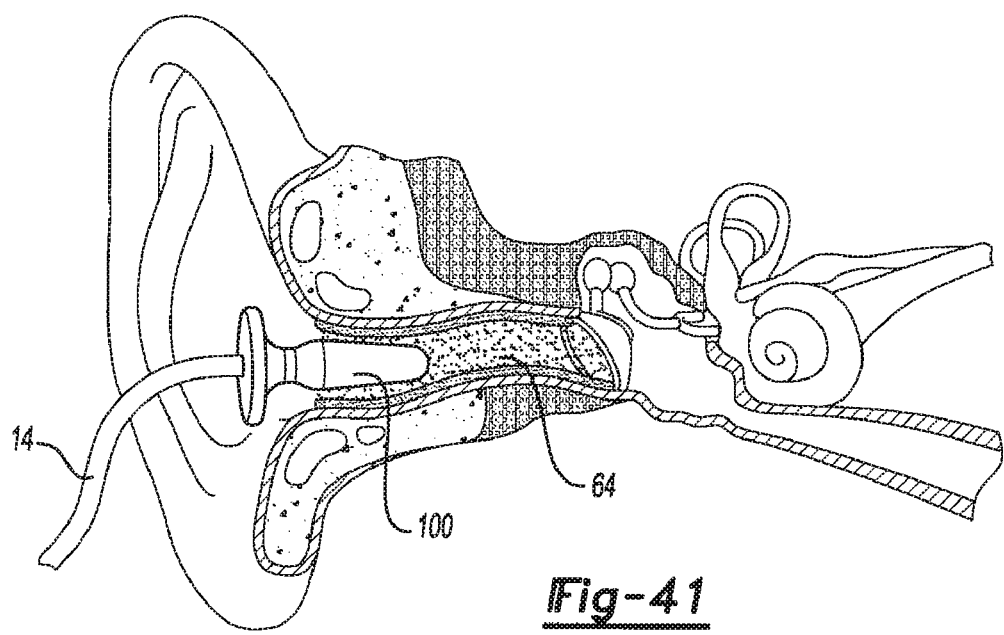
FIG. 41 is the same drawing as FIG. 37 but with the addition of another exemplary photodisinfection device in accordance to the principles of the present invention.

The method to treat otitis externa further includes applying light to the treatment site 64 at a wavelength absorbed by the photosensitizing composition so as to inhibit or eliminate microbes and/or to reduce inflammation at the treatment site 64. Microbes are defined herein to include any bacteria and/or fungi that contribute and cause otitis externa including but are not limited to *Pseudomonas aeruginosa, Staphylococcus aureus*, MRSA, *Aspergillus, Candida* or the like. The application of light can be delivered by: (1) the device (100 or 200) and the treatment system of the present invention (as shown in FIG. 41), (2) the optical probe disclosed in commonly owned PCT Patent Publication No. WO2006115761 (as shown in FIGS. 38 and 39), (3) the Periowave™ laser light system, and (4) any other art-disclosed suitable light delivery devices and/or systems.

As discussed above, the desired illumination pattern delivered by the device (100 or 200) for photodisinfection of the ear cavity is provided by at least one of the elements selected from the group consisting of: surface finish of the light dispersing section 18, geometry of the light dispersing section 18, surface finish of the member's 10 exterior surface, geometry of the member 10 and a combination thereof. Also, the light required for these methods is delivered to the device (100 or 200) by the light source 20 via the waveguide 14. As noted above, the surface finish and/or geometry of the distal end 16 of the waveguide 16 may also assist in providing the desired illumination pattern.

In the methylene blue embodiment, the wavelength preferably ranges from about 650 nm to 685 nm, more preferably from about 660 nm to about 680 nm, and most preferably at about 665 nm to about 675 nm. In the toluidine blue embodiment, the wavelength preferably ranges about 600 nm to about 670 nm, preferably from about 620 nm to 650 nm.

Depending on concentration of the photosensitizing composition 28 and the power of the light source 20, the application of light to the treatment site 64 may only require a short period of time such as from about 15 seconds to less than about 5 minutes, preferably from about 15 seconds to about two minutes, more preferably for about 30 seconds to about 90 seconds, and most preferably for about 30 seconds to 60 seconds. The light energy provided during each cycle of application of light is preferred to range from about 1 J/cm$^2$ to about 25 J/cm$^2$, more preferably at about 5 J/cm$^2$ to about 20 J/cm$^2$, and most preferably at about 6 J/cm$^2$ to about 12 J/cm$^2$. Depending on the nature and extent of the microbes located at the treatment site, the practitioner may apply multiple cycles of light applications (e.g., about 2 to about 10, about 3 to about 5, etc.) to the treatment site thereby resulting in a total accumulated light energy applied to treatment site that can be substantially higher than the light energy provided during each cycle. Again depending on the nature and extent of the microbes located at the treatment site, the entire method can be repeated multiple times (e.g., about 2 to about 10, about 3 to about 5, etc.) until the desired effects have been reached. It is preferred that the selections of photosensitizer concentration, wavelength, and/or total accumulated light energy applied to treatment site will allow the methods of the present invention to kill over about 90%, more preferably over 95%, and most preferably over 99% of the target microbes at the treatment site. It is preferred that the application of light to the treatment site does not cause physiological damage to the host tissues at and/or surround the treatment site and/or the ear cavity.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes.

The following examples provided in accordance to the present invention are for illustrative purpose only and are not intended as being exhaustive or limiting of the invention.

EXAMPLE I

Photodisinfection treatments using methods contemplated by the present invention have been tested against MRSA, *Escherichia coli* (*E. coli*), and *Enterococcus fecalis* (*E. fecalis*) in vitro and reached high levels of disinfection in within seconds to one minute. Photosensitizing composition comprising of methylene blue at various concentrations ranging from about 0.005 wt % to 0.1 wt % was applied to biofilms of MRSA, *E. coli* and *E. fecalis* for about ten seconds. These biofilms were then illuminated by a laser light system at a wavelength of about 665 nm to about 675 nm for a period from about 0 seconds to about 60 seconds (e.g., accumulated energy level of about 0 J/cm² to about 9 J/cm²). The laser light system used was the Periowave™ system which includes a low-intensity laser with power at about 240 mW and the optical probe described in PCT Patent Publication No. WO2006115761. As the graph set forth in Table 2 below shows, such photodisinfection treatment with the photosensitizing composition comprising at least 0.02 wt % of methylene blue and illumination by using the laser light source for at least 15 seconds (e.g., illumination energy level of at least 2.25 J/cm²) reduced both MRSA and *E. coli* by at least three logs (e.g., over 90% of reduction of MRSA, *E. coli*, and *E. fecalis*). The data showed that MRSA, *E. coli* and *E. Fecalis* were effectively eliminated by photodisinfection with methylene blue and a low power laser, and that there were improved bacterial log reductions over the range of methylene blue concentrations tested from about 0.02 wt % up to about 0.1 wt %. It also showed that a relatively short contract time between the methylene blue and the biofilm prior to illumination (e.g., a few seconds) is sufficient.

TABLE 2

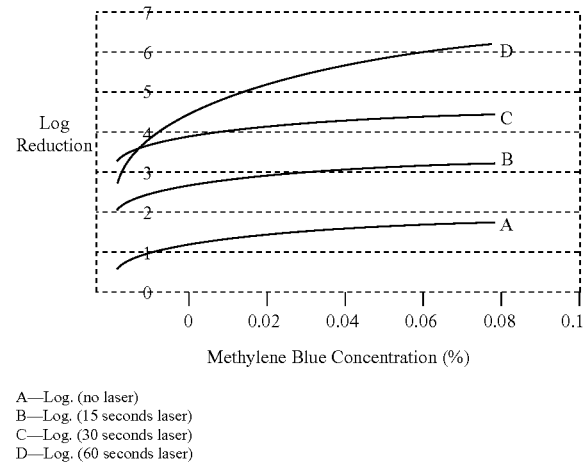

A—Log. (no laser)
B—Log. (15 seconds laser)
C—Log. (30 seconds laser)
D—Log. (60 seconds laser)

EXAMPLE II

Figure 33:
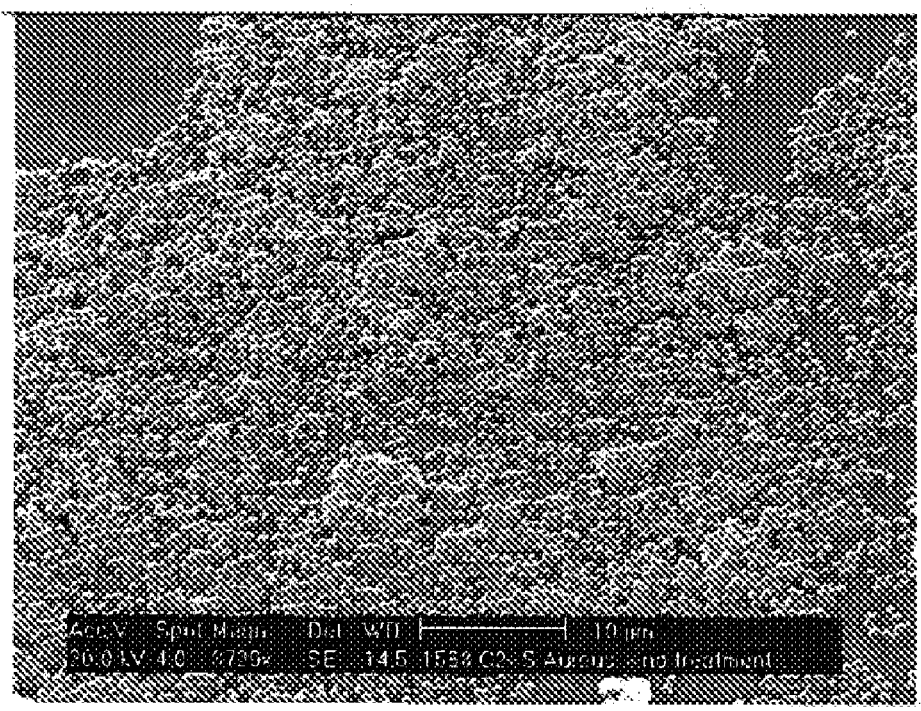
FIG. 33 is a SEM photograph of a colony of MRSA
Figure 34:
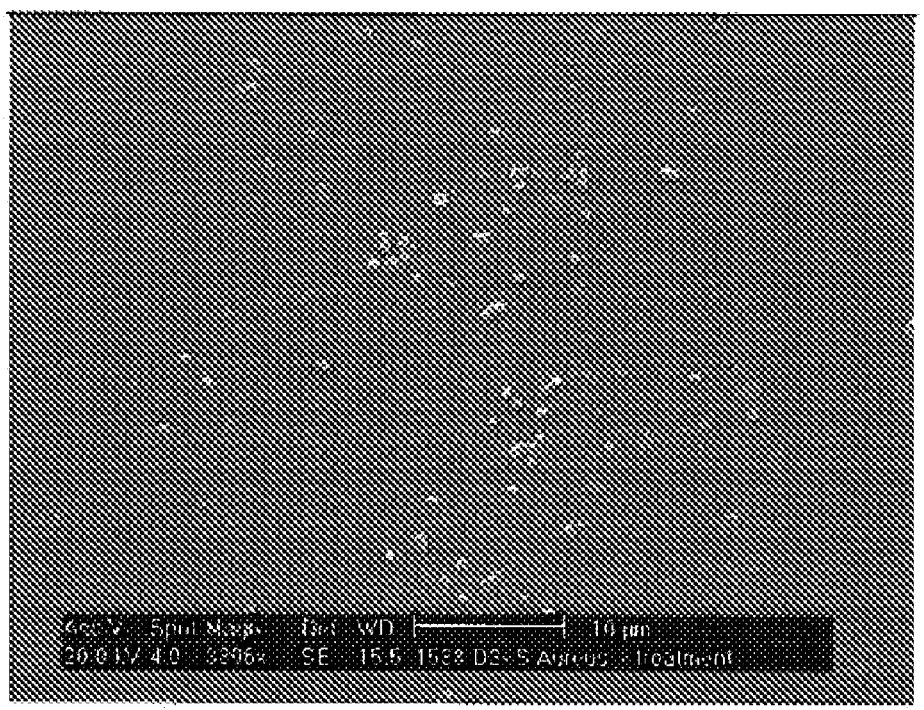
FIG. 34 is a SEM photograph of the colony of MRSA shown in FIG. 33 after treatment in accordance to the principles of the present invention.

Biofilms heavily colonized with one to four layers of MRSA organisms were contacted with a photosensitizing composition comprising methylene blue at a concentration of about 0.1 wt % for about 10 seconds and then illuminated at a wavelength of about 665 nm to about 675 nm for a period from about 30 seconds using the Periowave™ laser. Thereafter, these biofilms and the controlled MRSA biofilms (e.g., no photodisinfection treatment) were incubated overnight in 0.9 wt % saline and then fixed in 10 wt % Formalin for scanning electron microscope (SEM) evaluation. SEM photograph of a controlled MRSA biofilm is shown in FIG. 33. Comparing FIG. 33 to FIG. 34 which is a SEM photograph of a MRSA biofilm that has been subjected to the above-described photodisinfection treatment, there is clearly a substantial reduction of MRSA in FIG. 34.

EXAMPLE III

Figure 35:
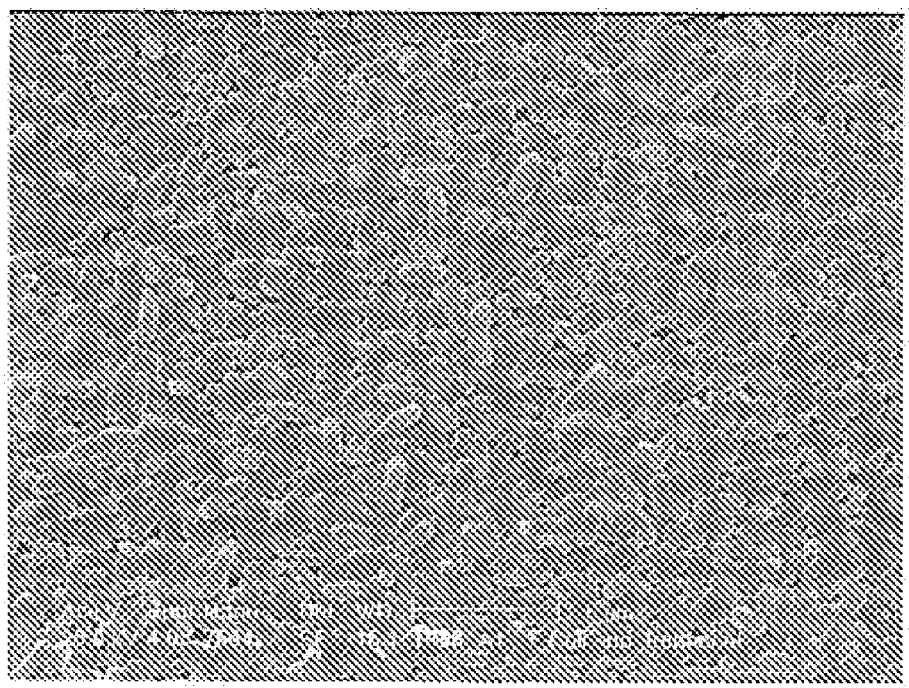
FIG. 35 is a SEM photograph of a colony of *E. coli*
Figure 36:
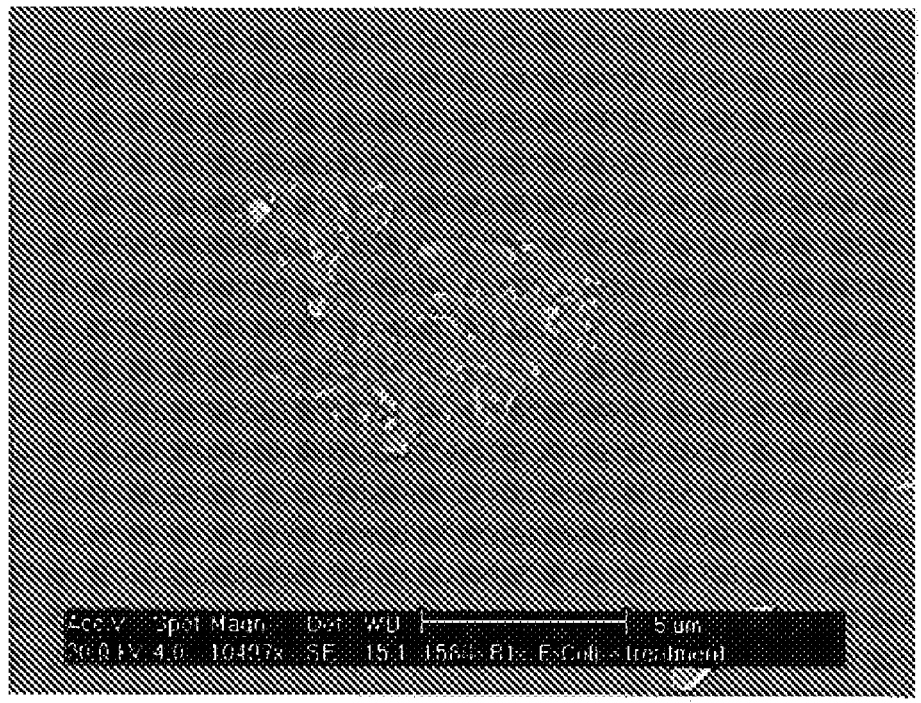
FIG. 36 is a SEM photograph of the colony of *E. coli* shown in FIG. 35 after treatment in accordance to the principles of the present invention.

Biofilms heavily colonized with one to three layers of *Escherichia coli* (*E. coli*) organisms were contacted with a photosensitizing composition comprising methylene blue at a concentration of about 0.1 wt % for about 10 seconds and then illuminated at a wavelength of about 665 nm to about 675 nm for a period from about 30 seconds using the Periowave™ laser. Thereafter, these biofilms and the controlled *E. coli* biofilms (e.g., no photodisinfection treatment) were incubated for three hours in 0.9% saline and then fixed in 10% Formalin for scanning electron microscope (SEM) evaluation. SEM photograph of a controlled *E. coli* biofilm is shown in FIG. 35. Comparing FIG. 35 to FIG. 36 which is a SEM photograph of an *E. coli* biofilm that has been subjected to the above-described photodisinfection treatment, there is clearly a substantial reduction of *E. coli* in FIG. 36.

EXAMPLE IV

Figure 40:
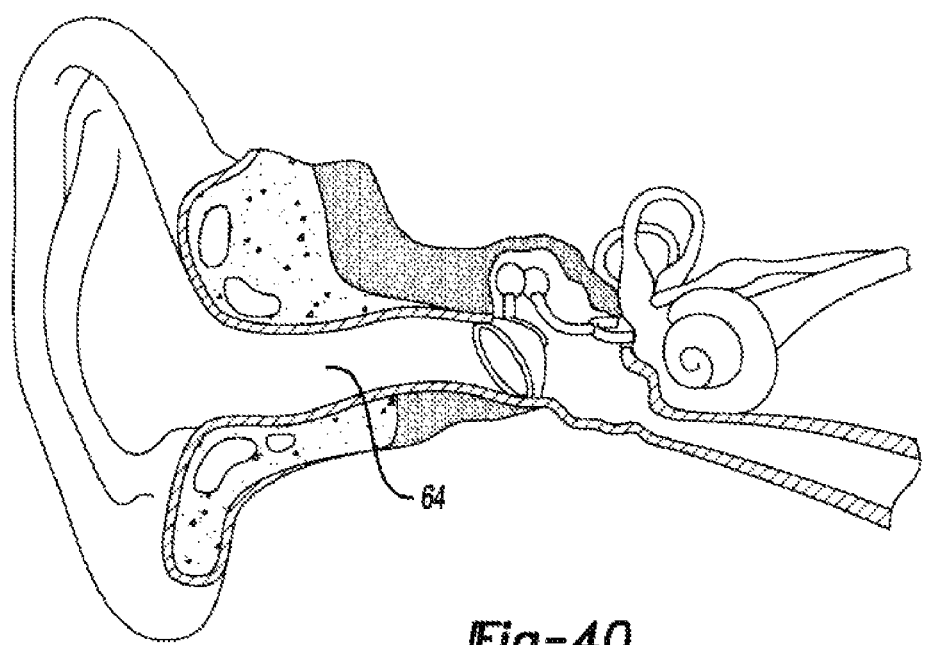
FIG. 40 is the same drawing as FIG. 37 with the absence of otitis externa and photosensitizing composition.

A study was conducted on patients suffering otitis externa. During the study, a photosensitizing composition comprising of methylene blue at a concentration of about 0.01 wt % was applied using a cotton swab to the treatment site as shown in FIG. 37. Thereafter and referring to FIGS. 38-39, light at a wavelength range from about 665 nm to about 675 nm was applied to the photosensitizing composition located within the treatment site 64 for a period from about 3 minutes to about 5 minutes (3-5 repetitive one minute cycles) using the Periowave™ laser light system. Many patients' otitis externa was ameliorated as shown in FIG. 40. For patients that suffered severe otitis externa, additional treatments (e.g., about 2 to about 5) using the same protocol as described in this paragraph were performed over a period of about one to about two weeks and such patients' otitis externa was also ameliorated.

EXAMPLE V

A photosensitizing composition comprising of methylene blue at a concentration of about 0.1 wt % is applied to the otitis externa treatment site. Light at a wavelength range from about 650 nm to about 680 nm is applied to the photosensitizing composition located within the otitis externa treatment site for a period from about 6 minutes to about 10 minutes using a laser with power at about 80 mW. The otitis externa was ameliorated.

EXAMPLE VI

A photosensitizing composition comprising of methylene blue at a concentration range of from about 0.001 wt % to about 0.1 wt % is applied to the otitis externa treatment site. Light at a wavelength range from about 650 nm to about 680 nm is applied to the photosensitizing composition located within the treatment site for a period from about 1 minute to about 20 minutes using a laser with power at a range from about 50 mW to about 300 mW. The otitis externa was ameliorated.

EXAMPLE VII

A photosensitizing composition comprising of toluidine blue at a concentration range of from about 0.001% wt % to about 0.1 wt % is applied to the otitis externa treatment site. Light at a wavelength range from about 620 nm to about 650 nm is applied to the photosensitizing composition located within the otitis externa treatment site for a period from about 1 minute to about 20 minutes using a laser with power at a range from about 50 mW to about 300 mW. The otitis externa was ameliorated.

For Examples V to VII, it was shown that there is a general inverse relationship between (1) the photosensitizer concentration and (2) the photodisinfection treatment time and/or the amount of power required for the light source. For example, higher concentration of photosensitizer requires less treatment time and/or lower light source power. Conversely, lower concentration of photosensitizer requires longer treatment time and/or higher light source power. Also, less treatment time requires higher concentration of photosensitizer and/or higher light source power.

What is claimed is:

1. A method of treating otitis externa comprising:
   (a) applying a photosensitizing composition to treatment site within ear cavity where microbes causing otitis externa are located;
   (b) inserting at least a portion of a light delivery device into the cavity; and
   (c) applying light to the treatment site at a wavelength absorbed by the photosensitizing composition so as to inhibit or eliminate the microbes and/or to reduce inflammation at the treatment site but without causing physiological damage to host tissue within the ear cavity; wherein
      (i) the light is delivery by the light delivery device to the treatment site;
      (ii) the light delivery device is in light communication with a light source via a waveguide;
      (iii) the photosensitizing composition comprises of toluidine blue at a concentration ranges from about 0.001 wt % to about 1 wt %; and
      (iv) the wavelength ranges from about 600 nm to 670 nm.

2. The method of claim 1 wherein the photosensitizing composition comprises of toluidine blue at a concentration ranges from about 0.001 wt % to about 0.1 wt %; the wavelength ranges from about 620 nm to about 650 nm and light energy provided by each of the application of light step to the treatment site ranges from about 6 J/cm$^2$ to about 12J/cm$^2$.

3. A method of treating otitis externa comprising;
   (a) applying a photosensitizing composition to treatment site within ear cavity where microbes causing otitis externa are located;
   (b) inserting at least a portion of a light delivery device into the cavity; and
   (c) applying light to the treatment site at a wavelength absorbed by the photosensitizing composition so as to inhibit or eliminate the microbes and/or to reduce inflammation at the treatment site but without causing physiological damage to host tissue within the ear cavity; wherein
      (i) the light is delivered by the light delivery device to the, treatment site:
      (ii) the light delivery device is light communication with a light source via a waveguide;
      (iii) the photosensitizing composition comprises of methylene blue at a concentration ranges from about 0.001 wt % to about 1 wt %; and
      (iv) the wavelength ranges from about 650 nm to 680 nm.

4. A method of treating otitis externa comprising:
   (a) applying a photosensitizing composition to treatment site within ear cavity where microbes causing otitis externa are located;
   (b) inserting at least a of a light deliver device into the cavity; and
   (c) applying light to the treatment site at a wavelength absorbed by the photosensitizing composition so as to inhibit or eliminate the microbes and or to reduce inflammation at the treatment site but without causing physiological damage to host tissue within the ear cavity; wherein
      (i) the light is delivered by the light delivery device to the treatment site;
      (ii) the light delivery device is in light Communication with a light source via a waveguide;
      (iii) the photosensitizing composition comprises of methylene blue at a concentration ranges from about 0.001 wt % to about 0.1 wt %;
      (iv) the wavelength ranges from about 665 nm to about 675 nm; and
      (v) light energy provided by each of the application of light step to the treatment site ranges from about 6J/cm$^2$ to about 12J/cm$^2$.

* * * * *

UNITED STATES PATENT AND TRADEMARK OFFICE
CERTIFICATE OF CORRECTION

PATENT NO. : 7,950,396 B2
APPLICATION NO. : 11/741604
DATED : May 31, 2011
INVENTOR(S) : Andreas Rose et al.

It is certified that error appears in the above-identified patent and that said Letters Patent is hereby corrected as shown below:

In Column 22 line 4 Claim 1 (c)(i) the word "delivery" should be "delivered" (1st occurrence)
In Column 22 line 43 Claim 4 (b) after "a" the word --portion-- should be inserted (1st occurrence)
In Column 22 line 43 Claim 4 (b) the word "deliver" should be "delivery"
In Column 22 line 47 Claim 4 (c) in between "and" "or" should be "/"
In Column 22 line 53 Claim 4 (c) (ii) the word "communication" should be with a lower case "c"

Signed and Sealed this
Twelfth Day of July, 2011

David J. Kappos
*Director of the United States Patent and Trademark Office*